(12) United States Patent
Jegla

(10) Patent No.: US 7,153,668 B2
(45) Date of Patent: Dec. 26, 2006

(54) HUMAN HAC3

(75) Inventor: Timothy J. Jegla, Durham, NC (US)

(73) Assignee: Icagen, Incorporated, Durham, NC (US)

( * ) Notice: Subject to any disclaimer, the term of this patent is extended or adjusted under 35 U.S.C. 154(b) by 715 days.

(21) Appl. No.: 09/548,933

(22) Filed: Apr. 13, 2000

(65) Prior Publication Data

US 2003/0044889 A1    Mar. 6, 2003

Related U.S. Application Data

(60) Provisional application No. 60/129,456, filed on Apr. 15, 1999.

(51) Int. Cl.
| | |
|---|---|
| *C12P 21/06* | (2006.01) |
| *C12N 1/20* | (2006.01) |
| *C07K 1/00* | (2006.01) |
| *C07H 21/02* | (2006.01) |
| *C07H 21/04* | (2006.01) |

(52) U.S. Cl. ............... 435/69.1; 435/320.1; 435/252.3; 536/23.1; 536/23.5; 530/350

(58) Field of Classification Search ..................... None
See application file for complete search history.

(56) References Cited

FOREIGN PATENT DOCUMENTS

| | | | |
|---|---|---|---|
| WO | WO 00/29448 | A2 | 5/2000 |
| WO | WO 00/29448 | A3 | 5/2000 |

OTHER PUBLICATIONS

Ludwig et al., 1998, Nature, 393, pp. 587-591.*

Ludwig, et al., "A family of hyperpolarization-activated mammalian cation channels"; *Nature*, vol. 393, p. 587-591, (Jun. 1998).

Santoro, et al., "Interactive cloning with the SH3 domain of N-src identifies a new brain specific ion channel protein, with homology to Eag and cyclic nucleotide-gated channels", *Proc. Natl. Acad. Sci. USA*, vol. 94, p. 14815-14820 (Dec. 1997).

Santoro, et al., "Identification of a Gene Encoding a Hyperpolarization-Activated Pacemaker Channel of Brain"; *Cell*, vol. 93, p. 717-729, (May 1998).

Frings, S. et al. "Characterization of ether-à-go-go channels present in photoreceptors reveals similarity to $I_{Kx}$, a $K^+$ current in rod inner segments," *J. Gen. Physiol.* Apr. 1998, pp. 583-599, vol. 131.

Jegla, T. et al. "Cloning and expression of a novel hyperpolarization-activated cation channel, human HCN3," *Society for neuroscience Abstracts, 29th Annual Meeting*; Miami Beach, Florida, USA Oct. 23-28, 1999, p. 1, Abstract No. 893.6.

Ludwig, A. et al. "Two pacemaker channels from human heart with profoundly different activation kinetics," *EMBO J.* May 4, 1999, pp. 2323-2329, vol. 18, No. 9.

Santoro, B. and Tibbs, G.R. "The HCN gene family: molecular basis of the hyperpolerization-activated pacemaker channels," *Annals of the New York Academy of Sciences* Apr. 30, 1999, pp. 741-764, vol. 868.

* cited by examiner

*Primary Examiner*—Olga N. Chernyshev
(74) *Attorney, Agent, or Firm*—Townsend and Townsend and Crew, LLP

(57) ABSTRACT

The invention provides isolated nucleic acid and amino acid sequences of hHAC3, antibodies to hHAC3, methods of detecting hHAC3, and methods of screening for modulators hyperpolarization-activated cation channels using biologically active hHAC3. The invention further provides, in a computer system, a method of screening for mutations of human HAC3 genes as well as a method for identifying a three-dimensional structure of human HAC3 polypeptides.

10 Claims, 6 Drawing Sheets

```
  1   MEA---EQREAAGASEGATPGLEAVEEVAEEPAT------------------------------------                    hHac3.pro
  1   ------------------------------------------------------------                              hHac2.pro
  1   MDARGGGGREGESPGATPAEGPPPPPEEAPEEGPGPAPPQHPPRAEALPPEAADEGGPRGR                              hHac1.pro 32   ------------------------------------------------------AASGP                               hHac3.pro
  1   ------------------------------------------------------------                              hHac2.pro
 61   LRSRDSSCGRPGTPGAASTAKGSPNGECCGRGEPQCSPAGPEGPARGPKVSFSCRGAASGP                              hHac1.pro 37   IEKSGP-----------REHLGTLLQETVNKFSLRVEGSHKAVEIEQE                                           hHac3.pro
  1   -----------EEK-----RHLGTLLQETVNKFSLRVEGSHKAVEIEQE                                          hHac2.pro
121   AEGPGEAFEEAGSEEAGPAGEPRGSQASFMQRQFGALLQEGVNKFSLRMEGSQKAVEREQE                              hHac1.pro 77   RVKSAGAWIIHPYSDFRFYWDLIMLIIMVGNLIVLPVGITFFKEENSPPWIVFNVLSDTF                               hHac3.pro
  5   RVKTAGFWIIHPYSDFRFYWDLIMIIMVGNLIMILPVGITFFEQITTPWIIFNVASDIV                                hHac2.pro
181   RVKSAGAWIIHPYSDFRFYWDFTMLLFMVGNLIIIPVGITFFKDETTAPWIVFNVMSDTF                               hHac1.pro 137   FLLDLVLNFRTGIVEEGAEIILAERAQRTRYLRTWELVDLISSIPVDYIFLVELEPRL                                 hHac3.pro
 65   FLLDLIMNFRTGIVNEDSSEILLDEKVLKMNYIKSWFVVDFISSIPVDYIFLTLIVEKG--M                             hHac2.pro
241   FIMDLVLNFRTGIVIEDNTEIILDEKLKKYLRTWFVVDEMSSIPVDYIFLIVEKG--I                                 hHac1.pro 197   DAFEVYKTARALRIVRFTKILSLLRLLRLSRLLIRYIHQWEEIFHMTYDLASAVVRIFNLIG                              hHac3.pro
123   DSEVYKTARALRIVRFTKILSLLRLLRLSRLLIRYIHQWEEIFHMTYDLASAVVRIFNLIG                              hHac2.pro
299   DSEVYKTARALRIVRFTKILSLLRLLRLSRLLIRYIHQWEEIFHMTYDLASAVMRIQNLIS                              hHac1.pro 257   MMLLLCHWDFCLQFLVPMLQDFPPDCWVSINHMVNHSWGRQYSHALFKAMSHMLCIGYGQ                                hHac3.pro
183   MMLLLCHWDFCLQFLVPLLQDFPPDCWVSINEMVNDSWGKQYSYALFKAMSHMLCIGYGA                                hHac2.pro
359   MMLLLCHWDFCLQFLVPMLQDFPRNCWVSINGMVNHSWSELYSFALFKAMSHMLCIGYGR                                hHac1.pro 317   QAPVGMEDVWLTMLSMIVGATCYAMFIGHATALIQSLDSSRRQYQEKYKQVEQYMSFHKL                                hHac3.pro
243   QAPVSMSDIWITMLSMIVGATCYAMFIGHATALIQSLDSSRRQYQEKYKQVEQYMSFHKL                                hHac2.pro
419   QAFESMIDIWLTMLSMIVGATCYAMFIGHATALIQSLDSSRRQYQEKYKQVEQYMSFHKL                                hHac1.pro
```

FIG. 1A.

```
377 PADTRQRIHEYYEHRYQGKMFDEESILGEISEPLREEILNFICRGLVAHMPLFAHADRSF  hHac3.pro
303 PADMRQKIHDYYEHRYQGKMFDEENILNELNDPLREEIVNFNCRKLVATMPLFANADPNF  hHac2.pro
479 PADFRQKIHDYYEHRYQGKMFDEDSILGELNGPLREEIVNENCRKLVASMPLFANADPNE  hHac1.pro 437 VTAMLTKLRFEVFQPGDLVVREGSVGRKMYFIZHGLISVLARGARDTRLTDGSYFGEICL  hHac3.pro
363 VTAMLSKLRFEVFQPGDYIIREGAVGKKMYFIZHGVAGMITKSSKEMKLTDGSYFGEICL  hHac2.pro
539 VTAMLTKLRFEVFQPGDYIIREGTIGKKMYFIZHGVVSVLTKGNKEMKLSDGSYFGEICL  hHac1.pro 497 LTRGRRTASVRADTYCRLYSLSVDHFNAVLEEEPMMRRAFETVAMDRILRIGKKNSILQR  hHac3.pro
423 LTKGRRTASVRADTYCRLYSLSVDNFNEVLEEYPMMRRAFETVAIDRLDRIGKKNSILLQ  hHac2.pro
599 LTRGRRTASVRADTYCRLYSLSVDNFNEVLEEYPMMRRAFETVAIDRLDRIGKKNSILLH  hHac1.pro 557 K-RSEPSPGL---SSGGIMEQHLVQHDRDMARGVRGRAPSTGAQLSGKPVLWEFLVHAPLQ  hHac3.pro
483 KFQKDLNTGVFNNQENELKQIVKHDREMVQAIAPINYPQMTTLNSTSTTTETSRMRTQ   hHac2.pro
459 KVQHDLNSGVFNNQENAHIQELVKYDREMVQA---ELGQRVGL-                hHac1.pro 613 AAAVTSNVAIALTHQRGPLELSP-DSPATIIARSAWRSAGSPA---SPLVPVR--AGPW  hHac3.pro
543 SPPMYTATSLSHSNLHSPSPSTQTPQESAILSPCSYTTAVCSPPVQSPLAARTFHYASPT  hHac2.pro
700 ------------FPPPPPPEQVTSAIATLQQAA-AMSFC-EQVARPLVGP-LALGSPR   hHac1.pro 666 ASTSRLRAE-PARTLHASLSRAGRSQVSLLGPPEGGG---------------GRRLGPR  hHac3.pro
603 ASQLSLMQQQPQQVQQSPQPRQPQQF-SPQPQTPGSSTPKNEVHKSTQAIHNTNLTRE  hHac2.pro
743 LVRRPPEGEAPAAASPGPPPPAASPRGALASERAPRTSPYGGLPAAPLAGPALPARRLSRA  hHac1.pro 709 GRPLSASQPSLPQRATGDGSPGRKGSGS---ERI----------PPSGLIAKPPPRTAQPP--  hHac3.pro
662 VRPESAMQPSLPHEVS--TLISRHPTVGESLASIPQPVTAVPGTGLQAGGRSRIVPQRVT  hHac2.pro
803 SRPLSASQPSLPHGAPGAPPPAASTREASSTPRLGPTEAARAAAPSPDRRDSASPGAAGGL-  hHac1.pro 756 --RPPVPERATPRGLQLSANM.                                       hHac3.pro
720 FFRQMSSGAIPENRGVIPAPLPLITHPHKK                               hHac2.pro
862 ------DEQDSARSRLSSNL.                                        hHac1.pro
```

FIG. 1B.

| whole brain | amygdala | caudate nucleus | cere- bellum | cerebral cortex | frontal lobe | hippo- campus | medulla oblongata |
|---|---|---|---|---|---|---|---|
| occipital lobe | putamen | substantia nigra | temporal lobe | thalamus | nucleus accumbeus | spinal cord | |
| heart | aorta | skeletal muscle | colon | bladder | uterus | prostate | stomach |
| testis | ovary | pancreas | pituitary gland | adrenal gland | thyroid gland | salivary gland | mammary gland |
| kidney | liver | small intestine | spleen | thymus | peripheral leukocyte | lymph node | bone marrow |
| appendix | lung | trachea | placenta | | | | |
| fetal brain | fetal heart | fetal kidney | fetal liver | fetal spleen | fetal thymus | fetal lung | |

*FIG. 2B.*

SEQUENCE LISTING

<160> NUMBER OF SEQ ID NOS: 16

<210> SEQ ID NO 1
<211> LENGTH: 774
<212> TYPE: PRT
<213> ORGANISM: Homo sapiens
<220> FEATURE:
<223> OTHER INFORMATION: human hyperpolarization-activated voltage-gated
      cation channel 3 (HAC3)

<400> SEQUENCE: 1

Met Glu Ala Glu Gln Arg Pro Ala Ala Gly Ala Ser Glu Gly Ala Thr
 1               5                  10                  15

Pro Gly Leu Glu Ala Val Pro Val Ala Pro Pro Ala Thr Ala
                20                  25                  30

Ala Ser Gly Pro Ile Pro Lys Ser Gly Pro Glu Pro Lys Arg Arg His
            35                  40                  45

Leu Gly Thr Leu Leu Gln Pro Thr Val Asn Lys Phe Ser Leu Arg Val
    50                  55                  60

Phe Gly Ser His Lys Ala Val Glu Ile Glu Gln Glu Arg Val Lys Ser
65                  70                  75                  80

Ala Gly Ala Trp Ile Ile His Pro Tyr Ser Asp Phe Arg Phe Tyr Trp
                85                  90                  95

Asp Leu Ile Met Leu Leu Leu Met Val Gly Asn Leu Ile Val Leu Pro
            100                 105                 110

Val Gly Ile Thr Phe Phe Lys Glu Glu Asn Ser Pro Pro Trp Ile Val
        115                 120                 125

Phe Asn Val Leu Ser Asp Thr Phe Phe Leu Leu Asp Leu Val Leu Asn
    130                 135                 140

Phe Arg Thr Gly Ile Val Val Glu Glu Gly Ala Glu Ile Leu Leu Ala
145                 150                 155                 160

Pro Arg Ala Ile Arg Thr Arg Tyr Leu Arg Thr Trp Phe Leu Val Asp
                165                 170                 175

Leu Ile Ser Ser Ile Pro Val Asp Tyr Ile Phe Leu Val Val Glu Leu
            180                 185                 190

Glu Pro Arg Leu Asp Ala Glu Val Tyr Lys Thr Ala Arg Ala Leu Arg
        195                 200                 205

Ile Val Arg Phe Thr Lys Ile Leu Ser Leu Leu Arg Leu Leu Arg Leu
    210                 215                 220

Ser Arg Leu Ile Arg Tyr Ile His Gln Trp Glu Glu Ile Phe His Met
225                 230                 235                 240

Thr Tyr Asp Leu Ala Ser Ala Val Val Arg Ile Phe Asn Leu Ile Gly
                245                 250                 255

Met Met Leu Leu Leu Cys His Trp Asp Gly Cys Leu Gln Phe Leu Val
            260                 265                 270

Pro Met Leu Gln Asp Phe Pro Pro Asp Cys Trp Val Ser Ile Asn His
        275                 280                 285

Met Val Asn His Ser Trp Gly Arg Gln Tyr Ser His Ala Leu Phe Lys
    290                 295                 300

Ala Met Ser His Met Leu Cys Ile Gly Tyr Gly Gln Gln Ala Pro Val
305                 310                 315                 320

Gly Met Pro Asp Val Trp Leu Thr Met Leu Ser Met Ile Val Gly Ala
                325                 330                 335

Thr Cys Tyr Ala Met Phe Ile Gly His Ala Thr Ala Leu Ile Gln Ser

-continued

```
                340                 345                 350
Leu Asp Ser Ser Arg Arg Gln Tyr Gln Glu Lys Tyr Lys Gln Val Glu
            355                 360                 365

Gln Tyr Met Ser Phe His Lys Leu Pro Ala Asp Thr Arg Gln Arg Ile
        370                 375                 380

His Glu Tyr Tyr Glu His Arg Tyr Gln Gly Lys Met Phe Asp Glu Glu
385                 390                 395                 400

Ser Ile Leu Gly Glu Leu Ser Glu Pro Leu Arg Glu Ile Ile Asn
                405                 410                 415

Phe Thr Cys Arg Gly Leu Val Ala His Met Pro Leu Phe Ala His Ala
            420                 425                 430

Asp Pro Ser Phe Val Thr Ala Val Leu Thr Lys Leu Arg Phe Glu Val
            435                 440                 445

Phe Gln Pro Gly Asp Leu Val Val Arg Glu Gly Ser Val Gly Arg Lys
            450                 455                 460

Met Tyr Phe Ile Gln His Gly Leu Leu Ser Val Leu Ala Arg Gly Ala
465                 470                 475                 480

Arg Asp Thr Arg Leu Thr Asp Gly Ser Tyr Phe Gly Glu Ile Cys Leu
            485                 490                 495

Leu Thr Arg Gly Arg Arg Thr Ala Ser Val Arg Ala Asp Thr Tyr Cys
            500                 505                 510

Arg Leu Tyr Ser Leu Ser Val Asp His Phe Asn Ala Val Leu Glu Glu
            515                 520                 525

Phe Pro Met Met Arg Arg Ala Phe Glu Thr Val Ala Met Asp Arg Leu
            530                 535                 540

Leu Arg Ile Gly Lys Lys Asn Ser Ile Leu Gln Arg Lys Arg Ser Glu
545                 550                 555                 560

Pro Ser Pro Gly Ser Ser Gly Gly Ile Met Glu Gln His Leu Val Gln
            565                 570                 575

His Asp Arg Asp Met Ala Arg Gly Val Arg Gly Arg Ala Pro Ser Thr
            580                 585                 590

Gly Ala Gln Leu Ser Gly Lys Pro Val Leu Trp Glu Pro Leu Val His
            595                 600                 605

Ala Pro Leu Gln Ala Ala Val Thr Ser Asn Val Ala Ile Ala Leu
            610                 615                 620

Thr His Gln Arg Gly Pro Leu Pro Leu Ser Pro Asp Ser Pro Ala Thr
625                 630                 635                 640

Leu Leu Ala Arg Ser Ala Trp Arg Ser Ala Gly Ser Pro Ala Ser Pro
            645                 650                 655

Leu Val Pro Val Arg Ala Gly Pro Trp Ala Ser Thr Ser Arg Leu Pro
            660                 665                 670

Ala Pro Pro Ala Arg Thr Leu His Ala Ser Leu Ser Arg Ala Gly Arg
            675                 680                 685

Ser Gln Val Ser Leu Leu Gly Pro Pro Gly Gly Gly Arg Arg
            690                 695                 700

Leu Gly Pro Arg Gly Arg Pro Leu Ser Ala Ser Gln Pro Ser Leu Pro
705                 710                 715                 720

Gln Arg Ala Thr Gly Asp Gly Ser Pro Gly Arg Lys Gly Ser Gly Ser
            725                 730                 735

Glu Arg Leu Pro Pro Ser Gly Leu Leu Ala Lys Pro Pro Arg Thr Ala
            740                 745                 750

Gln Pro Pro Arg Pro Pro Val Pro Glu Pro Ala Thr Pro Arg Gly Leu
            755                 760                 765
```

```
Gln Leu Ser Ala Asn Met
    770

<210> SEQ ID NO 2
<211> LENGTH: 2325
<212> TYPE: DNA
<213> ORGANISM: Homo sapiens
<220> FEATURE:
<223> OTHER INFORMATION: human hyperpolarization-activated voltage-gated
      cation channel 3 (HAC3)

<400> SEQUENCE: 2
atggaggcag agcagcggcc ggcggcgggg gccagcgaag gggcgacccc tggactggag      60
gcggtgcctc ccgttgctcc cccgcctgcg accgcggcct caggtccgat ccccaaatct     120
gggcctgagc ctaagaggag gcaccttggg acgctgctcc agcctacggt caacaagttc     180
tcccttcggg tgttcggcag ccacaaagca gtggaaatcg agcaggagcg ggtgaagtca     240 gcggggcct ggatcatcca ccctacagc gacttccggt tttactggga cctgatcatg      300
ctgctgctga tggtggggaa cctcatcgtc ctgcctgtgg catcaccctt cttcaaggag     360
gagaactccc cgccttggat cgtcttcaac gtattgtctg atactttctt cctactggat     420
ctggtgctca acttccgaac gggcatcgtg gtggaggagg tgctgagat cctgctggca      480 ccgcgggcca tccgcacgcg ctacctgcgc acatggttcc tggttgacct catctcttct     540
atccctgtgg attacatctt cctagtggtg gagctggagc acggttgga cgctgaggtc      600 tacaaaacgg cacgggccct acgcatcgtt cgcttcacca agatcctaag cctgctgagg     660
ctgctccgcc tctcccgcct catccgctac atacaccagt gggaggagat cttttcacatg     720 acctatgacc tggccagtgc tgtggttcgc atcttcaacc tcattgggat gatgctgctg     780
ctatgtcact gggatggctg tctgcagttc ctggtgccca tgctgcagga cttccctccc     840
gactgctggg tctccatcaa ccacatggtg aaccactcgt ggggccgcca gtattcccat     900
gccctgttca aggccatgag ccacatgctg tgcattggct atgggcagca ggcacctgta     960
ggcatgcccg acgtctggct caccatgctc agcatgatcg taggtgccac atgctacgcc    1020
atgttcatcg gccatgccac ggcactcatc cagtccctgg actcttcccg cgtcagtac     1080 caggagaagt acaagcaggt ggagcagtac atgtccttcc acaagctgcc agcagacacg    1140
cggcagcgca tccacgagta ctatgagcac cgctaccagg gcaagatgtt cgatgaggaa    1200
agcatcctgg gcgagctgag cgagccgctt cgcgaggaga tcattaactt cacctgtcgg    1260
ggcctggtgg cccacatgcc gctgtttgcc catgccgacc ccagcttcgt cactgcagtt    1320
ctcaccaagc tgcgctttga ggtcttccag ccggggatc tcgtggtgcg tgagggctcc    1380
gtggggagga agatgtactt catccagcat gggctgctca gtgtgctggc ccgcggcgcc    1440
cgggacacac gcctcaccga tggatcctac tttggggaga tctgcctgct aactaggggc    1500
cggcgcacag ccagtgttcg ggctgacacc tactgccgcc tttactcact cagcgtggac    1560
catttcaatg ctgtgcttga ggagttcccc atgatgcgcc gggcctttga gactgtggcc    1620
atggatcggc tgctccgcat cggcaagaag aattccatac tgcagcggaa gcgctccgag    1680
ccaagtccag cagcagtgg tggcatcatg gagcagcact tggtgcaaca tgacagagac    1740
atggctcggg gtgttcgggg tcgggccccg agcacaggag ctcagcttag tggaaagcca    1800
gtactgtggg agccactggt acatcgcgcc cttcaggcag ctgctgtgac ctccaatgtg    1860
gccattgccc tgactcatca gcggggcccct ctgccctct cccctgactc tccagccacc    1920
```

```
ctccttgctc gctctgcttg gcgctcagca ggctctccag cttccccgct ggtgcccgtc    1980
cgagctggcc catgggcatc cacctcccgc ctgcccgccc cacctgcccg aaccctgcac    2040
gccagcctat cccgggcagg gcgctcccag gtctccctgc tggtcccccc tccaggagga    2100
ggtggacggc ggctaggacc tcggggccgc ccactctcag cctcccaacc ctctctgcct    2160
cagcgggcaa caggcgatgg ctctcctggg cgtaagggat caggaagtga gcggctgcct    2220
ccctcagggc tcctggccaa acctccaagg acagcccagc cccccaggcc accagtgcct    2280
gagccagcca cacccgggg tctccagctt tctgccaaca tgtaa                     2325

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 3
cagccatgga ggcagagcag cggc                                           24

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:
      amplification primer

<400> SEQUENCE: 4
ggaggagatc tttcacatga catacgac                                       28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 5
agtaggatcc atcggtgagg cgtg                                           24

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      amplification primer

<400> SEQUENCE: 6
ttacatgttg gcagaaagct ggagacc                                        27

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:degenerate
      amplification primer
<221> NAME/KEY: modified_base
<222> LOCATION: (24)
<223> OTHER INFORMATION: n = g, a, c or t

<400> SEQUENCE: 7
```
tgggaggaga tcttycayat gacntayga 29

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:degenerate
      amplification primer
<221> NAME/KEY: modified_base
<222> LOCATION: (16)
<223> OTHER INFORMATION: n = g, a, c or t
<221> NAME/KEY: modified_base
<222> LOCATION: (25)
<223> OTHER INFORMATION: n = g, a, c or t

<400> SEQUENCE: 8
cgtctcgaat gccckn ckca tcatngg 27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:first round
      5' RACE gene specific primer

<400> SEQUENCE: 9
cctgctgccc atagccaatg cacagc 26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:second round
      nested 5' RACE gene specific primer

<400> SEQUENCE: 10
gcaccacgaa ctgcagacag ccatc 25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:nested 3'
      RACE gene specific reamplification primer

<400> SEQUENCE: 11
gttctcacca agctgcgctt tgaggtc 27

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:nested 3'
      RACE gene specific primer

<400> SEQUENCE: 12
ccagcatggg ctgctcagtg tgctg 25

<210> SEQ ID NO 13
<211> LENGTH: 25
<212> TYPE: DNA
<213> ORGANISM: Artificial Sequence -continued

```
<220> FEATURE:
<223> OTHER INFORMATION: Description of Artificial Sequence:nested 3'
      RACE gene specific primer

<400> SEQUENCE: 13
gcccactctc agcctcccaa ccctc                                            25

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:nested 3'
      RACE gene specific primer

<400> SEQUENCE: 14
cccaaccaag cttgcctcag cgggcaacag gcgatgg                               37

<210> SEQ ID NO 15
<211> LENGTH: 875
<212> TYPE: PRT
<213> ORGANISM: Homo sapiens
<220> FEATURE:
<223> OTHER INFORMATION: human hyperpolarization-activated voltage-gated
      cation channel 1 (HAC1)

<400> SEQUENCE: 15

Met Asp Ala Arg Gly Gly Gly Gly Arg Pro Gly Glu Ser Pro Gly Ala
  1               5                  10                  15

Thr Pro Ala Pro Gly Pro Pro Pro Pro Pro Ala Pro Pro Gln Gln Gly
                 20                  25                  30

Pro Gly Pro Ala Pro Pro Gln His Pro Pro Arg Ala Glu Ala Leu Pro
             35                  40                  45

Pro Glu Ala Ala Asp Glu Gly Gly Pro Arg Gly Arg Leu Arg Ser Arg
         50                  55                  60

Asp Ser Ser Cys Gly Arg Pro Gly Thr Pro Gly Ala Ala Ser Thr Ala
 65                  70                  75                  80

Lys Gly Ser Pro Asn Gly Glu Cys Gly Arg Gly Glu Pro Gln Cys Ser
                 85                  90                  95

Pro Ala Gly Pro Glu Gly Pro Ala Arg Gly Pro Lys Val Ser Phe Ser
            100                 105                 110

Cys Arg Gly Ala Ala Ser Gly Pro Ala Pro Gly Pro Gly Pro Ala Glu
            115                 120                 125

Glu Ala Gly Ser Glu Glu Ala Gly Pro Ala Gly Glu Pro Arg Gly Ser
        130                 135                 140

Gln Ala Ser Phe Met Gln Arg Gln Phe Gly Ala Leu Leu Gln Pro Gly
145                 150                 155                 160

Val Asn Lys Phe Ser Leu Arg Met Phe Gly Ser Gln Lys Ala Val Glu
                165                 170                 175

Arg Glu Gln Glu Arg Val Lys Ser Ala Gly Ala Trp Ile Ile His Pro
            180                 185                 190

Tyr Ser Asp Phe Arg Phe Tyr Trp Asp Phe Thr Met Leu Leu Phe Met
            195                 200                 205

Val Gly Asn Leu Ile Ile Ile Pro Val Gly Ile Thr Phe Phe Lys Asp
        210                 215                 220

Glu Thr Thr Ala Pro Trp Ile Val Phe Asn Val Val Ser Asp Thr Phe
225                 230                 235                 240

Phe Leu Met Asp Leu Val Leu Asn Phe Arg Thr Gly Ile Val Ile Glu
                245                 250                 255
```

-continued

```
Asp Asn Thr Glu Ile Ile Leu Asp Pro Glu Lys Ile Lys Lys Lys Tyr
            260                 265                 270

Leu Arg Thr Trp Phe Val Val Asp Phe Val Ser Ser Ile Pro Val Asp
            275                 280                 285

Tyr Ile Phe Leu Ile Val Glu Lys Gly Ile Asp Ser Glu Val Tyr Lys
            290                 295                 300

Thr Ala Arg Ala Leu Arg Ile Val Arg Phe Thr Lys Ile Leu Ser Leu
305                 310                 315                 320

Leu Arg Leu Leu Arg Leu Ser Arg Leu Ile Arg Tyr Ile His Gln Trp
                    325                 330                 335

Glu Glu Ile Phe His Met Thr Tyr Asp Leu Ala Ser Ala Val Met Arg
                340                 345                 350

Ile Cys Asn Leu Ile Ser Met Met Leu Leu Cys His Trp Asp Phe
                355                 360                 365

Cys Leu Gln Phe Leu Val Pro Met Leu Gln Asp Phe Pro Arg Asn Cys
            370                 375                 380

Trp Val Ser Ile Asn Gly Met Val Asn His Ser Trp Ser Glu Leu Tyr
385                 390                 395                 400

Ser Phe Ala Leu Phe Lys Ala Met Ser His Met Leu Cys Ile Gly Tyr
                    405                 410                 415

Gly Arg Gln Ala Pro Glu Ser Met Thr Asp Ile Trp Leu Thr Met Leu
                420                 425                 430

Ser Met Ile Val Gly Ala Thr Cys Tyr Ala Met Phe Ile Gly His Ala
            435                 440                 445

Thr Ala Leu Ile Gln Ser Leu Asp Ser Ser Arg Arg Gln Tyr Gln Glu
            450                 455                 460

Lys Tyr Lys Gln Val Glu Gln Tyr Met Ser Phe His Lys Leu Pro Ala
465                 470                 475                 480

Asp Phe Arg Gln Lys Ile His Asp Tyr Tyr Glu His Arg Tyr Gln Gly
                    485                 490                 495

Lys Met Phe Asp Glu Asp Ser Ile Leu Gly Glu Leu Asn Gly Pro Leu
                500                 505                 510

Arg Glu Glu Ile Val Asn Phe Asn Cys Arg Lys Leu Val Ala Ser Met
            515                 520                 525

Pro Leu Phe Ala Asn Ala Asp Pro Asn Phe Val Thr Ala Met Leu Thr
            530                 535                 540

Lys Leu Lys Phe Glu Val Phe Gln Pro Gly Asp Tyr Ile Ile Arg Glu
545                 550                 555                 560

Gly Thr Ile Gly Lys Lys Met Tyr Phe Ile Glx His Gly Val Val Ser
                    565                 570                 575

Val Leu Thr Lys Gly Asn Lys Glu Met Lys Leu Ser Asp Gly Ser Tyr
                580                 585                 590

Phe Gly Glu Ile Cys Leu Leu Thr Arg Gly Arg Thr Ala Ser Val
            595                 600                 605

Arg Ala Asp Thr Tyr Cys Arg Leu Tyr Ser Leu Ser Val Asp Asn Phe
610                 615                 620

Asn Glu Val Leu Glu Glu Tyr Pro Met Met Arg Arg Ala Phe Glu Thr
625                 630                 635                 640

Val Ala Ile Asp Arg Leu Asp Arg Ile Gly Lys Lys Asn Ser Ile Leu
                    645                 650                 655

Leu His Lys Val Gln His Asp Leu Asn Ser Gly Val Phe Asn Asn Gln
                660                 665                 670
```

-continued

```
Glu Asn Ala Ile Ile Gln Glu Ile Val Lys Tyr Asp Arg Glu Met Val
            675                 680                 685
Gln Gln Ala Glu Leu Gly Gln Arg Val Gly Leu Phe Pro Pro Pro Pro
        690                 695                 700
Pro Pro Pro Gln Val Thr Ser Ala Ile Ala Thr Leu Gln Gln Ala Ala
705                 710                 715                 720
Ala Met Ser Phe Cys Pro Gln Val Ala Arg Pro Leu Val Gly Pro Leu
                725                 730                 735
Ala Leu Gly Ser Pro Arg Leu Val Arg Arg Pro Pro Gly Pro Ala
            740                 745                 750
Pro Ala Ala Ala Ser Pro Gly Pro Pro Pro Ala Ser Pro Pro Gly
        755                 760                 765
Ala Pro Ala Ser Pro Arg Ala Pro Arg Thr Ser Pro Tyr Gly Gly Leu
770                 775                 780
Pro Ala Ala Pro Leu Ala Gly Pro Ala Leu Pro Ala Arg Arg Leu Ser
785                 790                 795                 800
Arg Ala Ser Arg Pro Leu Ser Ala Ser Gln Pro Ser Leu Pro His Gly
                805                 810                 815
Ala Pro Gly Pro Ala Ala Ser Thr Arg Pro Ala Ser Ser Ser Thr Pro
            820                 825                 830
Arg Leu Gly Pro Thr Pro Ala Ala Arg Ala Ala Ala Pro Ser Pro Asp
        835                 840                 845
Arg Arg Asp Ser Ala Ser Pro Gly Ala Ala Gly Gly Leu Asp Pro Gln
850                 855                 860
Asp Ser Ala Arg Ser Arg Leu Ser Ser Asn Leu
865                 870                 875

<210> SEQ ID NO 16
<211> LENGTH: 749
<212> TYPE: PRT
<213> ORGANISM: Homo sapiens
<220> FEATURE:
<223> OTHER INFORMATION: human hyperpolarization-activated voltage-gated
      cation channel 2 (HAC2) missing amino terminus

<400> SEQUENCE: 16

Lys Glu Gln Glu Arg Val Lys Thr Ala Gly Phe Trp Ile Ile His Pro
1               5                   10                  15
Tyr Ser Asp Phe Arg Phe Tyr Trp Asp Leu Ile Met Leu Ile Met Met
            20                  25                  30
Val Gly Asn Leu Val Ile Ile Pro Val Gly Ile Thr Phe Phe Thr Glu
        35                  40                  45
Gln Thr Thr Thr Pro Trp Ile Ile Phe Asn Val Ala Ser Asp Thr Val
    50                  55                  60
Phe Leu Leu Asp Leu Ile Met Asn Phe Arg Thr Gly Thr Val Asn Glu
65                  70                  75                  80
Asp Ser Ser Glu Ile Ile Leu Asp Pro Lys Val Ile Lys Met Asn Tyr
                85                  90                  95
Leu Lys Ser Trp Phe Val Val Asp Phe Ile Ser Ser Ile Pro Val Asp
            100                 105                 110
Tyr Ile Phe Leu Ile Val Glu Lys Gly Met Asp Ser Glu Val Tyr Lys
        115                 120                 125
Thr Ala Arg Ala Leu Arg Ile Val Arg Phe Thr Lys Ile Leu Ser Leu
    130                 135                 140
Leu Arg Leu Leu Arg Leu Ser Arg Leu Ile Arg Tyr Ile His Gln Trp
145                 150                 155                 160
```

-continued

```
Glu Glu Ile Phe His Met Thr Tyr Asp Leu Ala Ser Ala Val Val Arg
            165                 170                 175
Ile Phe Asn Leu Ile Gly Met Met Leu Leu Cys His Trp Asp Phe
        180                 185                 190
Cys Leu Gln Phe Leu Val Pro Leu Gln Asp Phe Pro Pro Asp Cys
        195                 200                 205
Trp Val Ser Leu Asn Glu Met Val Asn Asp Ser Trp Gly Lys Gln Tyr
        210                 215                 220
Ser Tyr Ala Leu Phe Lys Ala Met Ser His Met Leu Cys Ile Gly Tyr
225                 230                 235                 240
Gly Ala Gln Ala Pro Val Ser Met Ser Asp Leu Trp Ile Thr Met Leu
                245                 250                 255
Ser Met Ile Val Gly Ala Thr Cys Tyr Ala Met Phe Val Gly His Ala
                260                 265                 270
Thr Ala Leu Ile Gln Ser Leu Asp Ser Ser Arg Arg Gln Tyr Gln Glu
                275                 280                 285
Lys Tyr Lys Gln Val Glu Gln Tyr Met Ser Phe His Lys Leu Pro Ala
            290                 295                 300
Asp Met Arg Gln Lys Ile His Asp Tyr Tyr Glu His Arg Tyr Gln Gly
305                 310                 315                 320
Lys Ile Phe Asp Glu Glu Asn Ile Leu Asn Glu Leu Asn Asp Pro Leu
                325                 330                 335
Arg Glu Glu Ile Val Asn Phe Asn Cys Arg Lys Leu Val Ala Thr Met
                340                 345                 350
Pro Leu Phe Ala Asn Ala Asp Pro Asn Phe Val Thr Ala Met Leu Ser
            355                 360                 365
Lys Leu Arg Phe Glu Val Phe Gln Pro Gly Asp Tyr Ile Ile Arg Glu
        370                 375                 380
Gly Ala Val Gly Lys Lys Met Tyr Phe Ile Glx His Gly Val Ala Gly
385                 390                 395                 400
Val Ile Thr Lys Ser Ser Lys Glu Met Lys Leu Thr Asp Gly Ser Tyr
                405                 410                 415
Phe Gly Glu Ile Cys Leu Leu Thr Lys Gly Arg Arg Thr Ala Ser Val
                420                 425                 430
Arg Ala Asp Thr Tyr Cys Arg Leu Tyr Ser Leu Ser Val Asp Asn Phe
            435                 440                 445
Asn Glu Val Leu Glu Glu Tyr Pro Met Met Arg Arg Ala Phe Glu Thr
450                 455                 460
Val Ala Ile Asp Arg Leu Asp Arg Ile Gly Lys Lys Asn Ser Ile Leu
465                 470                 475                 480
Leu Gln Lys Phe Gln Lys Asp Leu Asn Thr Gly Val Phe Asn Asn Gln
                485                 490                 495
Glu Asn Glu Ile Leu Lys Gln Ile Val Lys His Asp Arg Glu Met Val
            500                 505                 510
Gln Ala Ile Ala Pro Ile Asn Tyr Pro Gln Met Thr Thr Leu Asn Ser
        515                 520                 525
Thr Ser Ser Thr Thr Thr Pro Thr Ser Arg Met Arg Thr Gln Ser Pro
530                 535                 540
Pro Val Tyr Thr Ala Thr Ser Leu Ser His Ser Asn Leu His Ser Pro
545                 550                 555                 560
Ser Pro Ser Thr Gln Thr Pro Gln Pro Ser Ala Ile Leu Ser Pro Cys
                565                 570                 575
```

-continued

```
Ser Tyr Thr Thr Ala Val Cys Ser Pro Pro Val Gln Ser Pro Leu Ala
            580             585             590

Ala Arg Thr Phe His Tyr Ala Ser Pro Thr Ala Ser Gln Leu Ser Leu
            595             600             605

Met Gln Gln Gln Pro Gln Gln Gln Val Gln Gln Ser Gln Pro Pro Gln
    610             615             620

Arg Gln Pro Gln Gln Pro Ser Pro Gln Pro Gln Thr Pro Gly Ser Ser
625             630             635             640

Thr Pro Lys Asn Glu Val His Lys Ser Thr Gln Ala Leu His Asn Thr
            645             650             655

Asn Leu Thr Arg Glu Val Arg Pro Phe Ser Ala Trp Gln Pro Ser Leu
            660             665             670

Pro His Glu Val Ser Thr Leu Ile Ser Arg Pro His Pro Thr Val Gly
            675             680             685

Glu Ser Leu Ala Ser Ile Pro Gln Pro Val Thr Ala Val Pro Gly Thr
            690             695             700

Gly Leu Gln Ala Gly Gly Arg Ser Thr Val Pro Gln Arg Val Thr Phe
705             710             715             720

Phe Arg Gln Met Ser Ser Gly Ala Ile Pro Pro Asn Arg Gly Val Leu
            725             730             735

Pro Ala Pro Leu Pro Leu Ile Thr Pro His Pro Lys Lys
            740             745
```

HUMAN HAC3

CROSS-REFERENCES TO RELATED APPLICATIONS

This application claims the benefit of U.S. Ser. No. 60/129,456, filed Apr. 15, 1999, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention provides isolated nucleic acid and amino acid sequences of hHAC3, antibodies to hHAC3, methods of detecting hHAC3, and methods of screening for modulators hyperpolarization-activated cation channels using biologically active hHAC3. The invention further provides, in a computer system, a method of screening for mutations of human HAC3 genes as well as a method for identifying a three-dimensional structure of human HAC3 polypeptides.

BACKGROUND OF THE INVENTION

A. General Background to Cation Channels

Cation channels are a diverse group of proteins that regulate the flow of cations across cellular membranes. The selectivity of a cation channel for particular cations typically varies with the valency of the cations, as well as the specificity of a given channel for a particular cation. Some cation channels display almost no selectivity for cations with the same valence (see, e.g., Saitow et al, *Biochim Biophys Acta* 1327(1):52–60 (1997)). Other channels are clearly selective for particular cations but are permeable to other cations to varying degrees (see, e.g., Park & MacKinnon, *Biochemistry* 34(41):13328–33 (1995) and Gauss et al., *Nature* 393(6685):583–7 (1998)).

Cation channels are involved in a number of physiological processes, including regulation of heartbeat, dilation of arteries, release of insulin, excitability of nerve cells, transduction of sensory stimuli, and regulation of renal electrolyte transport. Cation channels are thus found in a wide variety of animal cells such as nervous, muscular, glandular, immune, reproductive, sensory, and epithelial tissue. These channels allow the flow of various cations in and/or out of the cell under certain conditions. For example, the inward flow of cations upon opening of these channels makes the interior of the cell more positive, thus depolarizing the cell. These channels are regulated, e.g., by calcium sensitivity, voltage-gating, cyclic nucleotides or other secondary messengers, extracellular ligands, and ATP-sensitivity.

Certain classes of cation channels are formed by four alpha subunits and can be homomeric (made of identical alpha subunits) or heteromeric (made of two or more distinct types of alpha subunits). Some cation channels may contain other structurally distinct auxiliary, or beta, subunits. These subunits do not form potassium channels themselves, but instead modify the functional properties of channels formed by the alpha subunits. For example, the Kv beta subunits are cytoplasmic and are known to increase the surface expression of Kv channels and/or modify their inactivation kinetics (Heinemann et al., *J Phsyiol.* (Lond); 493:625–633; 1996 and Shi et al., *Neuron* 16(4):843–852, 1996). In another example, the KQT family beta subunit, minK, primarily changes activation kinetics (Sanguinetti et al., *Nature* 384: 80–83, 1996).

B. Hyperpolarization-activated Cation Channels: HAC1 and HAC2.

Specialized cells in the heart and brain can create rhythmic activity due in a large part to a depolarizing mixed sodium/potassium current known as $I_h$ (see, e.g., Santoro et al., *Cell* 93:717–729 (1998)). This pacemaker current is generated by hypolarization activated channels that are present in the heart (see, e.g., DiFrancesco, *Ann. Rev Physiol.* 55:455–72 (1993) and brain (see, e.g., Papa, *Ann. Rev. Physiol.* 58:299–327 (1996). In addition to contributing directly to rhythmic activity in the brain and heart, these channels may contribute significantly to resting membrane potentials in neurons and other cell types from a variety of tissues.

Recently a family of hyperpolarization-activated channels, given the acronym HAC, was isolated from mouse (see, Ludwig et al., *Nature* 393:587–91 (1998)). Ludwig et al. reported isolating three different ion channels (mHAC1, mHAC2 and mHAC3). The mouse HAC proteins are members of the voltage-gated cation channel super family and also have a cyclic nucleotide binding domain capable of binding cAMP and cGMP. Mouse HAC1 exhibits the general properties of $I_h$ and may be responsible for pacemaker activity.

Another group also identified the same gene family, in this instance identified by the acronym BCNG. For instance, the BCNG-1 (HAC2) ion channel was isolated from mouse cells and is expressed in the brain (see, e.g., Santoro et al, *Proc. Natl. Sci. USA* 94:14815–20 (1997)). The human BCNG-2/HAC1 and BCNG-1/HAC2 have also been cloned (see, e.g., Santoro et al., *Cell* 93:717–729 (1998)). Since then, several related mouse genes (e.g., BCNG-1/HAC2, partial BCNG2/HAC1, partial BCNG3/HAC4, and partial BCNG4/HAC3) with expression in various tissues, including heart and brain, have been isolated (see, e.g., Santoro et al., *Cell* 93:717–729 (1998)).

Phylogenetic analysis indicates that mHAC3 is more distantly related to mHAC1 or mHAC2 than are mHAC1 and mHAC2 to each other. Human HAC3 has not been previously isolated. Isolation of human HAC3 is therefore desirable, to better understand the physiology of HAC3 in humans and for the development of therapeutic and diagnostic applications to diseases related to hHAC3 in humans.

SUMMARY OF THE INVENTION

The current invention provides the first isolation and characterization of the human HAC3 cation channel, which has neither been previously cloned nor identified. The present invention provides both the nucleotide and amino acid sequence of hHAC3, as well as methods of assaying for modulators of hHAC3, antibodies to hHAC3, and methods of detecting hHAC3 nucleic acids and proteins.

The present invention provides an isolated nucleic acid encoding a polypeptide monomer comprising an alpha subunit of a cation channel wherein the polypeptide monomer has two attributes. First, the polypeptide monomer forms, with at least one additional HAC alpha subunit, a cation channel having the characteristic of activation upon hyperpolarization. Second, the polypeptide monomer has an amino acid sequence that has greater than about 75% identity to an N-terminal region (amino acids 1–50) of a human HAC3 amino acid sequence (e.g., SEQ ID NO:1) or greater than about 90% identity to amino acids 640–775 of a human HAC3 amino acid sequence (e.g., SEQ ID NO:1).

In one embodiment of the invention, the nucleic acid encodes SEQ ID NO:1. In another embodiment, the nucleic acid has a nucleotide sequence of SEQ ID NO:2. In yet another embodiment, the nucleic acid is a splice variant of SEQ ID NO:2.

In one embodiment of the invention includes a nucleic acid that is amplified by primers that selectively hybridize under stringent conditions to the same sequence as any two primers selected from CAGCCATGGAGGCAGAG-CAGCGGC (SEQ ID NO:3), GGAGGAGATCTTTCA-CATGACATACGAC (SEQ ID NO:4), AGTAGGATC-CATCGGTGAGGCGTG (SEQ ID NO:5), and TTACATGTTGGCAGAAAGCTGGAGACC (SEQ ID NO:6).

In one embodiment of the invention, the nucleic acid selectively hybridizes under moderately stringent hybridization conditions to the nucleotide of SEQ ID NO:2.

In one embodiment of the invention, the nucleic acid has a nucleotide sequence that has greater than about 90% identity to SEQ ID NO:2. In another embodiment, the nucleic acid encodes a polypeptide having an amino acid sequence that has greater than about 96% identity to SEQ ID NO:1.

The present invention also provides an isolated protein monomer comprising an alpha subunit of a cation channel wherein the polypeptide monomer 1) forms, with at least one additional HAC alpha subunit, a cation channel having the characteristic of activation upon hyperpolarization, and 2) has an amino acid sequence that has greater than about 75% identity to an N-terminal region (amino acids 1–50) or greater than about 90% identity to amino acids 640–775 of a human HAC3 amino acid sequence.

In one embodiment of the invention, the polypeptide monomer specifically binds to antibodies generated against SEQ ID NO:1.

In one embodiment, the isolated peptide monomer has an amino acid sequence of SEQ ID NO:1. In different embodiments, the isolated peptide monomer comprises either an alpha subunit of a homomeric or a heteromeric cation channel. In another embodiment, the isolated polypeptide monomer has a molecular weight between about 84 kDa and about 95 kDa. In yet another embodiment, the isolated polypeptide monomer has greater than about 96% identity to SEQ ID NO:1.

One aspect of the invention includes an antibody that selectively binds to a polypeptide monomer that 1) forms, with at least one additional HAC alpha subunit, a cation channel having the characteristic of activation upon hyperpolarization, and 2) has an amino acid sequence that has greater than about 75% identity to an N-terminal region (amino acids 1–50) or greater than about 90% identity to amino acids 640–775 of a human HAC3 amino acid sequence (e.g., SEQ ID NO:1).

The invention also provides for an expression vector comprising a nucleic acid encoding a polypeptide monomer comprising a subunit of a cation channel, wherein the cation channel (i) has the characteristic of activation upon hyperpolarization; and (ii) comprises a polypeptide monomer having an amino acid sequence that has greater than about 96% amino acid sequence identity to a human HAC3 amino acid sequence. In one embodiment, a host cell is transfected with the expression vector.

The invention also provides a method for identifying a compound that increases or decreases ion flux through a hyperpolarization-activated cation channel. The method comprises two steps. The first step comprises contacting the compound with a HAC polypeptide monomer. The polypeptide monomer 1) forms, with at least one additional HAC alpha subunit, a cation channel having the characteristic of activation upon hyperpolarization, and 2) has an amino acid sequence that has greater than about 75% identity to an N-terminal region (amino acids 1–50) or greater than about 90% identity to amino acids 640–775 of a human HAC3 amino acid sequence (e.g., SEQ ID NO:1). The second step of the method comprises determining the functional effect of the compound upon the cation channel.

In one embodiment, the functional effect is a physical effect or a functional effect. In another embodiment, the polypeptide is expressed in a eukaryotic host cell or cell membrane.

In one embodiment of the method, the functional effect is determined by measuring ion flux, or changes in current, voltage, ion concentrations, or yeast viability. In another embodiment, the isolated polypeptide monomer is recombinant. The method provides for a polypeptide monomer comprising an alpha subunit of either a homomeric or a heteromeric cation channel. Finally, in one aspect of the method, the polypeptide monomer has the amino acid sequence of SEQ ID NO:1.

In another aspect, the present invention provides a method of modulating ion flux through a human HAC channel, the method comprising the step of contacting the human HAC channel with a therapeutically effective amount of a compound identified as described above In another aspect, the present invention provides a method for identifying a compound that increases or decreases ion flux through a HAC potassium channel comprising a human HAC polypeptide, the method comprising the steps of: (i) entering into a computer system an amino acid sequence of at least 50 acids of a human HAC polypeptide or at least 150 nucleotides of a nucleic acid encoding the human HAC polypeptide, the human HAC polypeptide having an amino acid sequence that has greater than about 75% identity to amino acids 1–50 of SEQ ID NO:1 or greater than about 90% identity to amino acids 640–775 of SEQ ID NO:1; (ii) generating a three-dimensional structure of the polypeptide encoded by the amino acid sequence; (iii) generating a three-dimensional structure of the potassium channel comprising the human HAC polypeptide; (iv) generating a three-dimensional structure of the compound; and (v) comparing the three-dimensional structures of the polypeptide and the compound to determine whether or not the compound binds to the polypeptide.

The invention also provides for a method of detecting the presence of HAC3 in a sample. The method comprises the steps of: (i) isolating a biological sample; (ii) contacting the biological sample with a human HAC3-specific reagent that selectively associates with human HAC3; and, (iii) detecting the level of human HAC3-specific reagent that selectively associates with the sample.

In one embodiment, the human HAC3-specific reagent is selected from the group consisting of: human HAC3 specific antibodies, human HAC3 specific oligonucleotide primers, and human HAC3 nucleic acid probes.

The invention further provides for a method of screening for mutations of human HAC3 genes using a computer system. The method comprises (i) entering into a computer system a first nucleic acid sequence encoding an hyperpolarization-activated cation channel polypeptide monomer having a nucleotide sequence of SEQ ID NO:2, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences. In one embodiment of this method, the second nucleic acid sequence is associated with a disease state. The invention further provides a computer readable substrate comprising the first nucleic sequence as described in the above-described method. In one embodiment of this composition, the computer readable substrate further comprises the second nucleic acid as described in the above-described method.

Finally, the invention also provides a method for identifying a three-dimensional structure of human HAC3 polypeptide monomers. The method comprises (i) entering into a computer system an amino acid sequence of at least 60 amino acids of a polypeptide monomer or at least 180 nucleotides of a gene encoding the polypeptide monomer, the polypeptide monomer having an amino acid sequence of SEQ ID NO:1, and conservatively modified versions thereof; and (ii) generating a three-dimensional structure of the polypeptide monomer encoded by the amino acid sequence.

In one embodiment of this method, the amino acid sequence is a primary structure and the generating step includes the steps of (i) forming a secondary structure from said primary structure using energy terms determined by the primary structure; and (ii) forming a tertiary structure from said secondary structure using energy terms determined by said secondary structure. In another embodiment, the generating step also includes the step of forming a quaternary structure from the tertiary structure using anisotropic terms encoded by the tertiary structure. In another aspect of the method, the method also includes the step of identifying regions of the three-dimensional structure of a human HAC3 cation channel protein that bind to ligands and using the regions to identify ligands that bind to the cation channel. A further aspect of the invention includes a computer readable substrate comprising the tree dimensional structure derived from the above-described method.

BRIEF DESCRIPTION OF THE DRAWINGS

FIG. 1. Amino acid alignment of human Hac3 (SEQ ID NO:1) with human Hac1 (SEQ ID NO:15) and human Hac2 (SEQ ID NO:16). Identical residues are boxed. The numbers at the left edge indicated amino acid position. Note that the human Hac2 is missing the amino terminus.

DETAILED DESCRIPTION OF THE INVENTION

I. Introduction

Figure 2A:
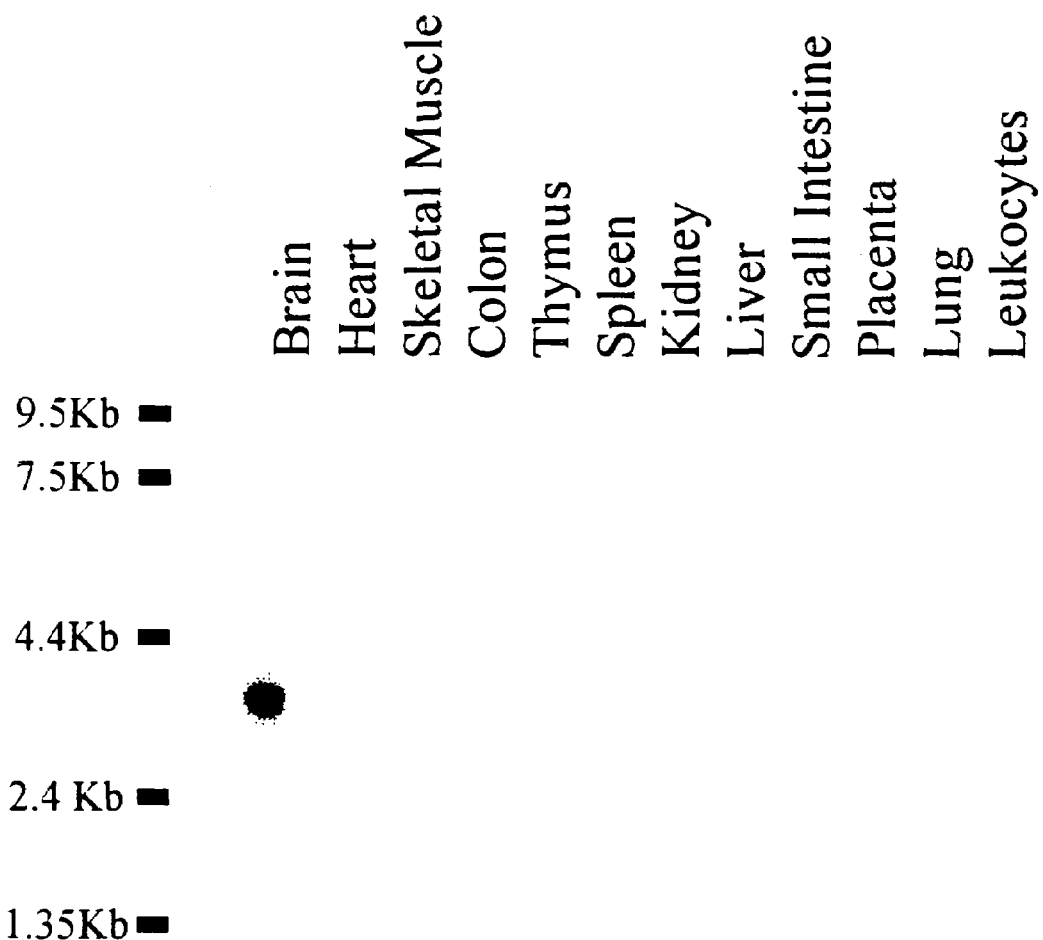
FIG. 2. Northern blot analysis of human Hac3. 2(A) Traditional northern blot of Hac3. A transcript of approximately 4 Kb is abundant in brain and also present in heart. Larger transcripts (approximately 5 Kb) are seen in brain, heart, liver and kidney. 2(B) mRNA dot blot northern of Hac3. Expression is most abundant in brain, but is widespread in peripheral tissues. Note that mRNA dot blots are several times more sensitive for detection of message than traditional northerns. Also note the wide discrepancy between the high level of message detected on the dot blot for small intestine and colon versus the lack of expression on the traditional northern. These tissues often label more highly on dot blots, and it is possible that this is an effect of poor mRNA quality for these tissues.
Figure 3A:
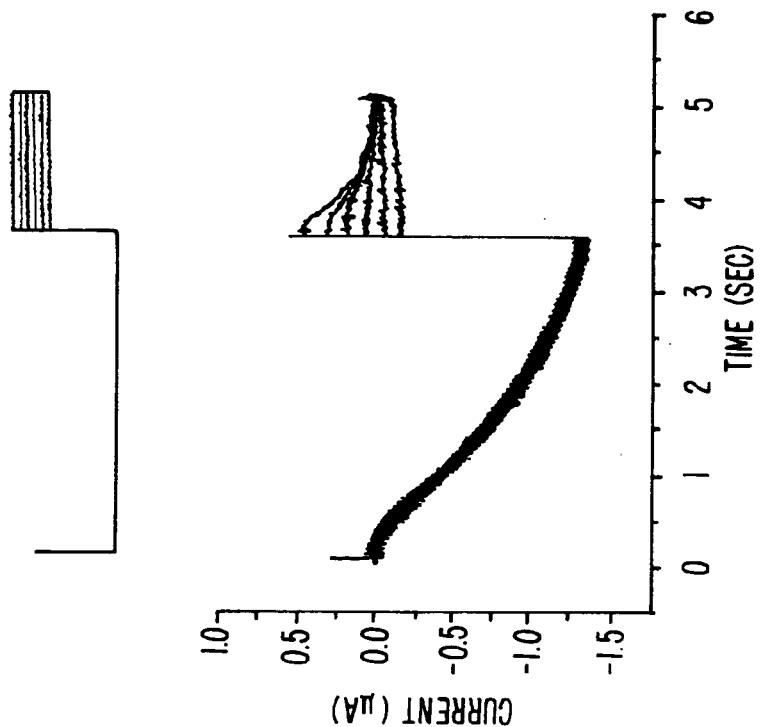
FIG. 3. Hac3 currents expressed in *Xenopus* oocytes. 3(A) Hac3 currents were elicited with 3.2 second pulses ranging from −70 to −160 mV in 10 mV increments from a holding potential of −30 mV. Outward tail currents were measured at 0 mV. 3(B) Hac3 currents were elicited by steps to −140 mV and tail currents were measured at repolarization steps ranging from −50 to 0 mV in 10 mV increments. The current reverses between −40 and −30 mV suggesting that Hac3 passes both sodium and potassium.
Figure 3B:
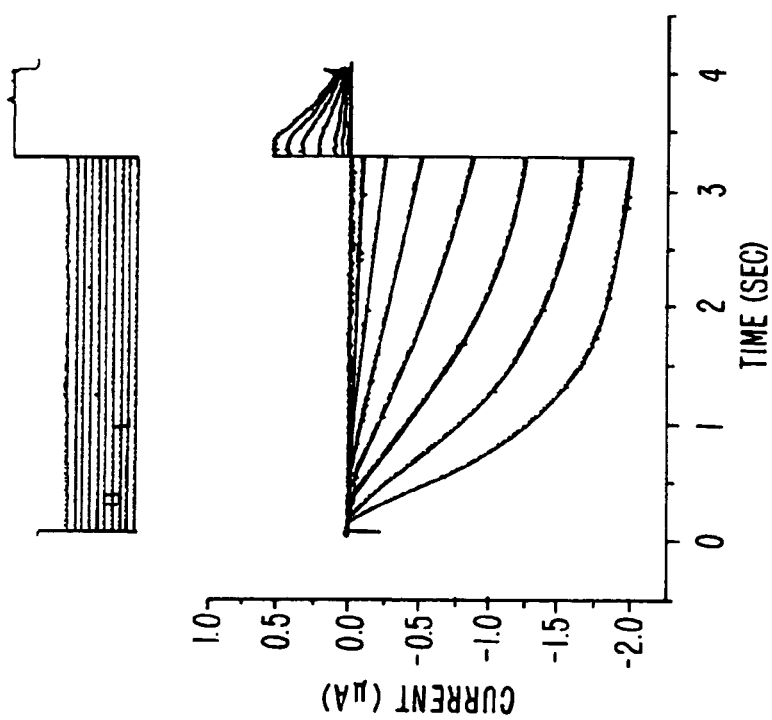
Figure 4:
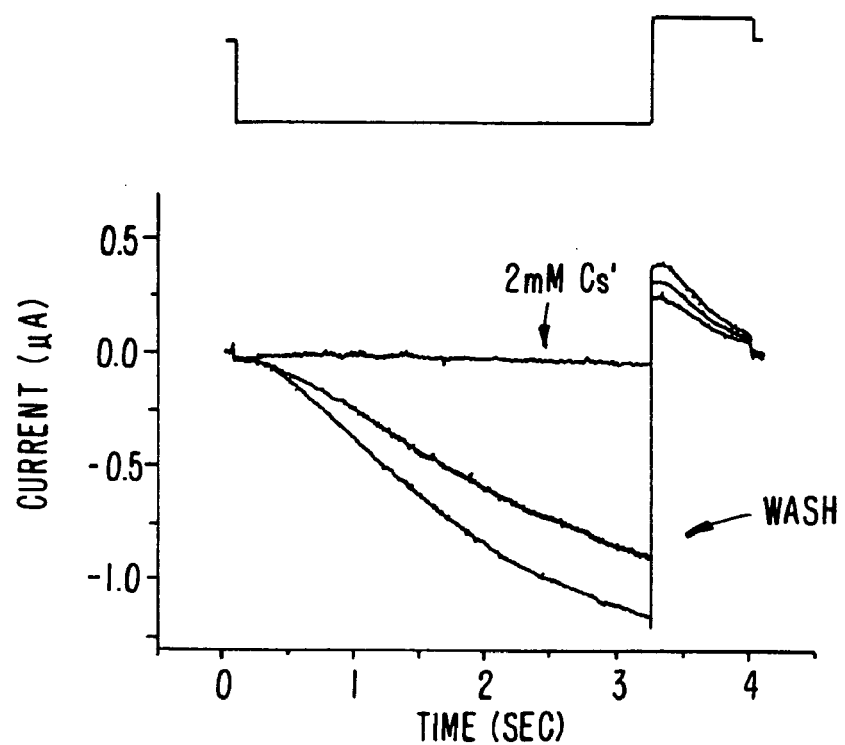
FIG. 4. Hac3 currents are blocked by Cesium. Hac3 currents were elicited by steps from −30 mV to −140 mV. Tail currents were measured at 0 mV. 2 mM $Cs^+$ completely blocked the inward Hac3 current measured at −140 mV, but had less effect on the outward tail current. This suggests that the Cs+ blocking site is in the external mouth of the Hac3 pore.

The present invention provides for the first time a nucleic acid encoding a human HAC3 alpha subunit, identified and cloned from human tissue. This polypeptide monomer is a member of the HAC family of potassium channel monomers and is most closely related to the CNG channel α-subunits and the "eag" (ether à go-go) subfamily of potassium channel monomers. Members of this family are voltage-gated cation channels with six membrane-spanning segments (S1–S6). These segments include a voltage sensing S4 segment and an ion conducting pore between S5 and S6. Voltage-gated cation channels have significant roles in maintaining the resting potential and in controlling excitability of a cell.

The invention also provides methods of screening for modulators of hyperpolarization-activated cation channels comprising a hHAC3 alpha subunit. For example, such modulators may alter the voltage-gating characteristic of hHAC. Hyperpolarization activated channels, such as those comprising hHAC3, have a greater probability of opening when the membrane comprising the channels is hyperpolarized. Modulators of hyperpolarization-activated channel activity may be useful for treating various pacemaker dysfunctions such as familial sinus rhythm diseases, sick sinus syndrome associated with atrial fibrillation, sinus tachycardias and bradycardias as well as ventricular arrhythmias. The modulators are also useful for treating other disorders involving abnormal ion flux, e.g., memory and learning disorders, sleeping disorders, bipolar disease, schizophrenia, CNS disorders such as migraines, hearing and vision problems, seizures, and as neuroprotective agents (e.g., to prevent stroke).

Furthermore, the invention provides assays for hHAC3 activity where hHAC3 acts as a direct or indirect reporter molecule. Human HAC3 can have broad application as a reporter molecule in assay and detection systems. For instance, hHAC3 can be used as a reporter molecule to measure changes in potassium or sodium concentration, membrane potential, current flow, ion flux, transcription, signal transduction, receptor-ligand interactions, second messenger concentrations, in vitro, in vivo, and ex vivo. In one embodiment, hHAC3 can be used as an indicator of current flow in a particular direction (e.g., outward or inward cation flow), and in another embodiment, hHAC3 can be used as an indirect reporter via attachment to a second reporter molecule such as green fluorescent protein.

The invention provides for methods of detecting hHAC3 nucleic acid and protein expression, allowing investigation of the channel diversity provided by hHAC3, as well as diagnosis of disease caused by pacemaker activity dysfunction such as familial sinus rhythm diseases, sick sinus syndrome associated with atrial fibrillation, sinus tachycardias, bradycardias and ventricular arrhythmias as well as abnormal ion flux, e.g., memory and learning disorders, sleeping disorders, bipolar disease, schizophrenia, CNS disorders such as migraines, hearing and vision problems, seizures.

Finally, the invention provides for a method of screening for mutations of hHAC3 genes or proteins. The invention includes, but is not limited to, methods of screening for mutations in hHAC3 with the use of a computer. Similarly, the invention provides for methods of identifying the three-dimensional structure of hHAC3, as well as the resulting computer readable images or data that comprise the three dimensional structure of hHAC3. Other methods for screening for mutations of hHAC genes or proteins include high density oligonucleotide arrays, PCR, immunoassays and the like.

Functionally, hHAC3 is an alpha subunit of a voltage-gated cation channel that is activated upon hyperpolarization. Voltage-gated channels are heteromeric or homomeric and typically contain four alpha subunits or monomers, each with six transmembrane domains. Heteromeric channels comprise one or more hHAC3 alpha subunits along with additional alpha subunits from the HAC family (e.g., HAC1 or HAC2). In addition, such channels may comprise one or more auxiliary beta subunits. At its carboxy terminus, hHAC3 also contains a sequence with similarity to cyclic nucleotide binding proteins. Therefore, it is likely that hHAC3 channel activity can be modulated by cyclic nucleotides such as cAMP or cGMP. The presence of hHAC3 in a cation channel may also modulate the activity of the channel and thus enhance channel diversity. Channel diversity is also enhanced with alternatively spliced forms of hHAC3. The cation channels may also include an auxiliary beta subunit that modulates channel activity and thus enhances channel diversity.

Structurally, the nucleotide sequence of human HAC3 (SEQ ID NO:2) encodes a polypeptide monomer of approximately 775 amino acids with a predicted molecular weight of 85–94 kDa. Human HAC3 contains six membrane spanning domains (S1–6), including a voltage sensing domain (S4) and an ion-conduction pore between S5 and S6, as well as a putative cyclic nucleotide binding domain region that has a conserved amino acid sequence. This entire region is located at approximately amino acids 53 to 554. Furthermore, hHAC3 contains an N-terminal domain located at amino acids 1 to 50, which provides a means for identifying alleles and conservatively modified variants of hHAC3. Alternatively, hHAC3 can be identified as a cation channel subunit polypeptide having 90% or more identity to the region defined by amino acids 640–775 of SEQ ID NO:1.

The present invention also provides polymorphic variants of hHAC3. For instance, in variant #1, an aspartate is substituted for a leucine at position 545. In variant #2, a valine is substituted for an isoleucine at amino acid position number 37. In variant #3, a threonine is substituted for an alanine at amino acid position 686. In variant #4, an alanine is substituted for a glycine at amino acid position 702.

Specific regions of hHAC3 amino acid and nucleotide sequences may be used to identify conservatively modified or polymorphic variants and alleles of hHAC3. This identification can be made in vitro, e.g., under stringent hybridization conditions and sequencing, or by using the sequence information in a computer system for comparison with other nucleotide sequences. Amino acid identity of approximately at least 96% or above, preferably 98%, most preferably 99% or above to the entire hHAC3 polypeptide (SEQ ID NO:1) or a portion thereof, typically demonstrates that a protein is a polymorphic variant or allele of hHAC3. The first 50 amino acid residues of SEQ ID NO:1 displays considerable variance relative to the mouse HAC3 N-terminus. Since this region is significantly different from other known HAC sequences, the first 50 amino acids of SEQ ID NO:1 are preferably used to differentiate sequences related to human HAC3 from HAC sequences from other species. Therefore, an amino acid identity of approximately 75% or above, preferably 80%, and most preferably 90% or above to the first 50 amino acids of SEQ ID NO:1 peptide demonstrates that a protein is a conservatively modified or polymorphic variant or allele of hHAC3. Alternatively, the conserved region of amino acids 640–775 of SEQ ID NO:1 can be used to identify conservatively modified variants, alleles, and polymorphic variants of hHAC3. Amino acid sequence identity of 90% or more to this conserved region demonstrates that a protein is a conservatively modified or polymorphic variant or allele of hHAC3.

Nucleotide identity of approximately at least 90%, preferably 95% and most preferably 98% or above to the entire hHAC3 nucleic acid sequence (SEQ ID NO:2) or portions thereof, typically demonstrates that a nucleic acid is a conservatively modified or polymorphic variant or allele of hHAC3. Alternatively, hHAC3 can be identified as a cation channel subunit polypeptide having 90% or more identity to the region defined by amino acids 640–775 of SEQ ID NO:1. Sequence comparison is performed using the sequence comparison algorithms discussed below, using the default parameters described below. Antibodies that bind specifically to the HAC3 subunit can also be used to identify alleles, conservatively modified or polymorphic variants. Finally, analysis of the three dimensional structure of the hHAC3 polypeptide can be used to predict alleles of hHAC3 that have conserved function.

Conservatively modified or polymorphic variants and alleles of hHAC3 are confirmed by expressing the putative hHAC3 polypeptide monomer either alone or co-expressed with another cation channel subunit and examining whether the monomer forms a cation channel. Functional assays may be used to determine the characteristics of the cation channels formed in such ways. One assay is to determine changes in cellular polarization by measuring changes in current (thereby measuring changes in polarization) with voltage-clamp and patch-clamp techniques, e.g., "the cell-attached" mode, "the inside-out" mode, and "the whole cell" mode (see, e.g., Ackerman et al., *New Engl. J. Med.* 336:1575–1595 (1997)). This assay is used to demonstrate that a cation channel comprising a polypeptide monomer having about 96% or greater, preferably 98% or greater amino acid identity to the entire sequence of hHAC3 or a portion thereof is a species of hHAC3 because the subunit shares the same functional characteristics. Typically, hHAC3 monomers having the amino acid sequence of SEQ ID NO:1 are used as positive controls in comparison to the putative hHAC3 protein to demonstrate the identification of a polymorphic variant or allele of hHAC3.

Human HAC3 nucleotide and amino acid sequence information may also be used to construct models of a hyperpolarization-activated cation channel in a computer system. These models are subsequently used to identify compounds that can activate or inhibit a hyperpolarization-activated cation channel comprising hHAC3. Such compounds that modulate the activity of channels comprising hHAC3 can be used to investigate the role of hHAC3 in modulation of channel activity and in channel diversity.

The identification and cloning of hHAC3 for the first time provides a means for assaying for inhibitors and activators of human hyperpolarization-activated cation channels such as cation channels comprising hHAC3. Biologically active hHAC3 is useful for testing inhibitors and activators of cation channels comprising hHAC3 and other hyperpolarization-activated cation channels using in vivo and in vitro expression that measure, e.g., changes in voltage or current. Such activators and inhibitors, identified using a voltage-gated cation channel comprising at least one hHAC3 monomer, can be used to further study, e.g., regulation of cation channels activated upon hyperpolarization, channel kinetics, and conductance properties of such channels. These activators and inhibitors are also useful as pharmaceutical agents for treating diseases involving pacemaker dysfunctions such as familial sinus rhythm diseases, sick sinus syndrome associated with atrial fibrillation, sinus tachycardias, bradycardias and ventricular arrhythmias as well as abnormal ion flux, e.g., memory and learning disorders, sleeping disorders, bipolar disease, schizophrenia, CNS disorders, as described above.

Methods of detecting hHAC3 and expression of channels comprising the hHAC3 monomers are also useful for diagnostic applications for diseases involving pacemaker dysfunctions such as familial sinus rhythm diseases, sick sinus syndrome associated with atrial fibrillation, sinus tachycardias, bradycardias and ventricular arrhythmias as well as abnormal ion flux, e.g., CNS disorders and other disorders. For example, chromosome localization of the gene encoding hHAC3 can be used to identify diseases caused by and associated with the hHAC3. Methods of detecting hHAC3 polypeptides are also useful for examining the role of the hHAC3 monomers in channel diversity and modulation of channel activity.

II. Definitions

As used herein, the following terms have the meanings ascribed to them unless specified otherwise.

Cation channels with the characteristic of "activation upon hyperpolarization" (also referred to as "hyperpolarization-activated") have a low probability of opening at cellular resting potentials (from about −50 mV to about −80 mV) and have an increasing probability of opening at more hyperpolarized potentials. Thus a cation channel having the characteristic of activation upon hyperpolarization will have a greater probability of opening at −100 mV than at −70 mV. Cation channels having the characteristic of activation upon hyperpolarization also open more quickly at more hyperpolarized potentials. Thus a cation channel having the characteristic of activation upon hyperpolarization will also open more quickly at −100 mV than at −70 mV. A discussion of activation by hyperpolarization can be found in Luthi & McCormick, *Neuron* 21(1):9–12 (1998).

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" is a polypeptide monomer that is an auxiliary subunit of a cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The term "transmembrane domain" refers to the region of the cation channel subunit polypeptide that spans across the lipid bilayer membrane of the cells. Various families of the cation channels have different numbers of transmembrane domains that travel across the cellular membrane. Structurally, a transmembrane domain starts from the first amino acid residue of the subunit sequence that enters into the cellular membrane and ends with the last amino acid residue in the subunit sequence that leaves the cellular membrane.

The phrase "voltage-gated" activity or "voltage-gating" refers to a characteristic of a HAC channel composed of individual polypeptide monomers or subunits. Generally, the probability of a voltage-gated HAC channel opening increases as a cell is hyperpolarized. The reversal potential for HAC channels is primarily determined by the reversal potentials of the two major permeant cations, sodium and potassium. $E_K$, or the reversal potential for potassium, depends on the relative concentrations of potassium found inside and outside the cell membrane, and is typically between −60 and −100 mV for mammalian cells. For example, $E_K$ is the membrane potential at which there is no net flow of potassium ion because the electrical potential (i.e., membrane potential) driving potassium influx is balanced by the concentration gradient directing potassium efflux. This value is also known as the "reversal potential" or the "Nernst" potential for potassium. Similarly, $E_{Na}$, or the reversal potential for sodium, depends on the relative concentration of sodium found inside and outside the cell and is typically near 50 mV. Because HAC channels pass both sodium and potassium, their reversal potential lies between $E_K$ and $E_{Na}$, and is typically −20 to −40 mV. Hyperpolarization activated cation channels primarily allow influx of cations because they have greater probabilities of being open at membrane potentials more negative than this equilibrium potential.

Certain hyperpolarization activated channels such as HAC channels are typically composed of four subunits and the channel can be heteromeric or homomeric. The characteristic of voltage gating can be measured by a variety of techniques for measuring changes in current flow and ion flux through a channel, e.g., by changing the [K⁺] of the external solution and measuring the activation potential of the channel current (see, e.g., U.S. Pat. No. 5,670,335), by measuring current with patch clamp techniques or voltage clamp under different conditions, and by measuring ion flux with radio-labeled tracers or voltage-sensitive dyes under different conditions.

"hHAC3" refers to a polypeptide that is an alpha subunit or monomer of a hyperpolarization-activated cation channel, a member of the HAC subfamily, and a member of the voltage-gated cation channel super family. The term hHAC3 therefore refers to conservatively modified variants, polymorphic variants, alleles, mutants that: (1) form cation channels that are voltage-gated and activated upon hyperpolarization; (2) specifically bind to polyclonal antibodies raised against an immunogen comprising an amino acid sequence selected from the group consisting of SEQ ID NO:1 and conservatively modified variants or portions thereof, including the N-terminal region (amino acids 1–50 of HAC3); (3) have at least about 75% identity to the N-terminal region of hHAC3 (amino acids 1–50 of HAC3);

or (4) are encoded by nucleic acids that are amplified by primers that specifically hybridize under stringent hybridization conditions to the same sequence as a primer set consisting of SEQ ID NO:3 and SEQ ID NO:4 or SEQ ID NO:5 and SEQ ID NO:6. Alternatively, hHAC3 can be identified as a cation channel subunit polypeptide having 90% or more identity to the region defined by amino acids 640–775 of SEQ ID NO:1.

The phrase "functional effects" in the context of assays for testing compounds affecting a channel comprising hHAC3 includes the determination of any parameter that is indirectly or directly under the influence of the channel. It includes changes in ion flux and membrane potential, and also includes other physiologic effects such increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., potassium, rubidium, sodium. Preferably, the term refers to the functional effect of the compound on the channels comprising hHAC3, e.g., changes in ion flux including radioisotopes, changes in ion concentration (e.g., $Ca^{2+}$, $K^+$, $Na^+$) current amplitude, membrane potential, current flow, transcription, protein binding, phosphorylation, dephosphorylation, second messenger concentrations (cAMP, cGMP, $Ca^{2+}$, $IP_3$), ligand binding, and other physiological effects such as hormone and neurotransmitter release, as well as changes in voltage and current. Such functional effects can be measured by any means known to those skilled in the art, e.g., patch clamping, voltage-sensitive dyes, whole cell currents, radioisotope efflux, inducible markers, and the like.

"Inhibitors," "activators" or "modulators" of hyperpolarization-activated voltage-gated cation channels comprising hHAC3 refer to inhibitory or activating molecules identified using in vitro and in vivo assays for hHAC3 cation channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing hHAC3 in cells or cell membranes and then measuring flux of ions through the channel and determining changes in polarization (i.e., electrical potential). To examine the extent of inhibition, samples or assays comprising a hyperpolarization-activated cation channel (e.g., hHAC3) are treated with a potential activator or inhibitor and are compared to control samples without the inhibitor. Control samples (untreated with inhibitors) are assigned a relative hHAC3 activity value of 100%. Inhibition of channels comprising hHAC3 is achieved when the hHAC3 activity value relative to the control is about 90%, preferably 50%, more preferably 25–0%. Activation of channels comprising hHAC3 is achieved when the hHAC3 activity value relative to the control is 110%, more preferably 150%, most preferably at least 200–500% higher or 1000% or higher.

"Biologically active" hHAC3 refers to hHAC3 that comprises a cation channel having the characteristic of activation upon hyperpolarization tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated hHAC3 nucleic acid is separated from open reading frames that flank the hHAC3 gene and encode proteins other than hHAC3. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants". Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of cation channel splice variants is discussed in Leicher, et al., *J Biol. Chem.* 273(52):35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide.

These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radio-label into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, or designated conserved region such as the N-terminal region, as measured using one of the following sequence comparison algorithms with the default parameters described below or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length, more preferably over the length of the reference amino acid sequence or nucleotide sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to human HAC3 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

An "anti-hHAC3" antibody is an antibody or antibody fragment that specifically binds a polypeptide encoded by the hHAC3 gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to hHAC3, encoded in SEQ ID NO:1, splice variants, or portions thereof, can be selected to obtain only those polyclonal antibodies that are specifically immunoreactive with hHAC3 and not with other proteins, except for polymorphic variants and alleles of hHAC3. This selection may be achieved by subtracting out antibodies that cross-react with molecules such as mouse HAC3 and other HAC3 orthologs. Other human members of the HAC family, such as human HAC1 and 2 can also be used to select for antibodies that recognize only human HAC3. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as E. coli, or eukaryotic cells such as yeast (e.g., Pichia), insect, amphibian, or mammalian cells such as CHO, HeLa and the like, e.g., cultured cells, explants, and cells in vivo.

"Biological sample" as used herein is a sample of biological tissue or fluid that contains hHAC3 or nucleic acid encoding hHAC3 protein. Such samples include, but are not limited to, tissue isolated from humans. Biological samples may also include sections of tissues such as frozen sections taken for histological purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating the Gene Encoding hHAC3

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding hHAC3

In general, the nucleic acid sequences encoding hHAC3 and related nucleic acid sequence homologs are cloned from cDNA and genomic DNA libraries or isolated using amplification techniques with oligonucleotide primers. For example, hHAC3 sequences are typically isolated from human nucleic acid (genomic or cDNA) libraries by hybridizing with a nucleic acid probe or polynucleotide, the sequence of which can be derived from SEQ ID NO:2.

A suitable tissue from which hHAC3 RNA and cDNA can be isolated is the putamen, thalamus, caudate nucleus, medulla, occipital lobe, substantia nigra, spinal cord, and fetal brain. See Example 1 for a complete list of the tissues in which hHAC3 is expressed.

Amplification techniques using primers can also be used to amplify and isolate hHAC3 from DNA or RNA. The following primers can also be used to amplify a sequence of hHAC3:

| | |
|---|---|
| CAGCCATGGAGGCAGAGCAGCGGC, | (SEQ ID NO:3) |
| GGAGGAGATCTTTCACATGACATACGAC, | (SEQ ID NO:4) |
| AGTAGGATCCATCGGTGAGGCGTG, | (SEQ ID NO:5) |
| TTACATGTTGGCAGAAAGCTGGAGACC. | (SEQ ID NO:6) |

These primers can be used, e.g., to amplify either the full length sequence or a probe of one to several hundred nucleotides, which is then used to screen a human library for full-length hHAC3.

Nucleic acids encoding hHAC3 can also be isolated from expression libraries using antibodies as probes. Such polyclonal or monoclonal antibodies can be raised using the sequence of SEQ ID NO:1.

Human HAC3 polymorphic variants and alleles that are substantially identical SEQ ID NO:2 can be isolated using hHAC3 nucleic acid probes and oligonucleotides under stringent hybridization conditions, by screening libraries. Alternatively, expression libraries can be used to clone hHAC3 and hHAC3 polymorphic variants and alleles by detecting expressed homologs immunologically with antisera or purified antibodies made against hHAC3 or portions thereof (e.g., the N-terminal region, amino acids 1–50 of HAC3), which also recognize and selectively bind to the hHAC3 homolog.

To make a cDNA library, one should choose a source that is rich in hHAC3 mRNA, e.g., tissue such as the thalamus, medulla or fetal brain. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating hHAC3 nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of hHAC3 directly from mRNA, from cDNA, from genomic libraries or cDNA libraries. Degenerate oligonucleotides can be designed to amplify hHAC3 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of hHAC3 encoding mRNA in physiological samples, for nucleic acid sequencing, or for other purposes. Genes amplified by the PCR reaction can be purified from agarose gels and cloned into an appropriate vector.

Gene expression of hHAC3 can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology and the like.

Synthetic oligonucleotides can be used to construct recombinant hHAC3 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the hHAC3 gene. The specific subsequence is then ligated into an expression vector.

The gene for hHAC3 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding hHAC3, one typically subclones hHAC3 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the hHAC3 protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the hHAC3 encoding nucleic acid in host cells. A typical expression cassette thus contains a promoter operably linked to the nucleic acid sequence encoding hHAC3 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a hHAC3 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of hHAC3 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing hHAC3.

After the expression vector is introduced into the cells, the transfected cells are cultured under conditions favoring expression of hHAC3, which is recovered from the culture using standard techniques identified below.

IV. Purification of hHAC3 Polypeptides

Either naturally occurring or recombinant hHAC3 can be purified for use in functional assays. Naturally occurring hHAC3 monomers can be purified, e.g., from mouse or human tissue such as thalamus, medulla or fetal brain tissue and any other source of a hHAC3 homolog. Recombinant hHAC3 monomers can be purified from any suitable expression system.

The hHAC3 monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant hHAC3 monomers are being purified. For example, proteins having established molecular adhesion properties can be reversible fused to the hHAC3 monomers. With the appropriate ligand, the hHAC3 monomers can be selectively adsorbed to a purification column and then freed from the column in a relatively pure form. The fused protein is then removed by enzymatic activity. Finally the hHAC3 monomers could be purified using immunoaffinity columns.

A. Purification of hHAC3 Monomers from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the hHAC3 monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human HAC3 monomers are separated from other bacterial proteins by standard separation techniques, e.g., with Ni-NTA agarose resin.

Alternatively, it is possible to purify the hHAC3 monomers from bacteria periplasm. After lysis of the bacteria, when the hHAC3 monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying the hHAC3 Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the hHAC3 monomers can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The hHAC3 monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of hHAC3

In addition to the detection of hHAC3 genes and gene expression using nucleic acid hybridization technology, one can also use immunoassays to detect the hHAC3 monomers. Immunoassays can be used to qualitatively or quantitatively analyze the hHAC3 monomers. A general overview of the applicable technology can be found in Harlow & Lane, *Antibodies: A Laboratory Manual* (1988).

A. Antibodies to hHAC3 Monomers

Methods of producing polyclonal and monoclonal antibodies that react specifically with the hHAC3 monomers are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of hHAC3 monomers may be used to produce antibodies specifically reactive with hHAC3 monomers. For example, recombinant hHAC3 monomers or an antigenic fragment thereof such as amino acids 1–50 or amino acids 640–775 of SEQ ID NO:1, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-hHAC3 proteins or even other related proteins from other organisms (e.g., other HAC family members), using a competitive binding immunoassay. Specific polyclonal antisera and monoclonal antibodies will usually bind with a $K_D$ of at least about 0.1 mM, more usually at least about 1 μM, preferably at least about 0.1 μM or better, and most preferably, 0.01 μM or better.

Once the specific antibodies against a hHAC3 are available, the hHAC3 can be detected by a variety of immunoassay methods. For a review of immunological and immunoassay procedures, see Basic and Clinical Immunology (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The hHAC3 can be detected and/or quantified using any of a number of well recognized immunological binding assays (see, e.g., U.S. Pat. Nos. 4,366,241; 4,376,110; 4,517, 288; and 4,837,168). For a review of the general immunoassays, see also Methods in Cell Biology: Antibodies in Cell Biology, volume 37 (Asai, ed. 1993); Basic and Clinical Immunology (Stites & Terr, eds., 7$^{th}$ ed. 1991). Immunological binding assays (or immunoassays) typically use an antibody that specifically binds to a protein or antigen of choice (in this case the hHAC3 or an antigenic subsequence thereof). The antibody (e.g., anti-hHAC3) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled hHAC3 polypeptide or a labeled anti-hHAC3 antibody. Alternatively, the labeling agent may be a third moiety, such a secondary antibody, which specifically binds to the antibody/hHAC3 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., J. Immunol. 111:1401–1406 (1973); Akerstrom et al., J. Immunol. 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting the hHAC3 in samples may be either competitive or noncompetitive. Noncompetitive immunoassays are assays in which the amount of antigen is directly measured. In one preferred "sandwich" assay, for example, the anti-hHAC3 subunit antibodies can be bound directly to a solid substrate on which they are immobilized. These immobilized antibodies then capture hHAC3 present in the test sample. The hHAC3 monomers are thus immobilized and then bound by a labeling agent, such as a second hHAC3 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the hHAC3 present in the sample is measured indirectly by measuring the amount of known, added (exogenous) hHAC3 displaced (competed away) from an anti-hHAC3 antibody by the unknown hHAC3 present in a sample. In one competitive assay, a known amount of the hHAC3 is added to a sample and the sample is then contacted with an antibody that specifically binds to the hHAC3. The amount of exogenous hHAC3 bound to the antibody is inversely proportional to the concentration of the hHAC3 present in the sample. In a particularly preferred embodiment, the antibody is immobilized on a solid substrate. The amount of hHAC3 bound to the antibody may be determined either by measuring the amount of hHAC3 present in a hHAC3/antibody complex, or alternatively by measuring the amount of remaining uncomplexed protein. The amount of hHAC3 may be detected by providing a labeled hHAC3 molecule.

A hapten inhibition assay is another preferred competitive assay. In this assay the known hHAC3 is immobilized on a solid substrate. A known amount of anti-hHAC3 antibody is added to the sample, and the sample is then contacted with the immobilized hHAC3. The amount of anti-hHAC3 antibody bound to the known immobilized hHAC3 is inversely proportional to the amount of hHAC3 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations for hHAC3. For example, a protein at least partially encoded by SEQ ID NO:2 or an immunogenic region thereof, such as the N-terminal region (amino acids 1–50), can be immobilized to a solid support. Other proteins such as other HAC family members, e.g., mouse HAC3 or human HAC1 or HAC2, are added to the assay so as to compete for binding of the antisera to the immobilized antigen. The ability of the added proteins to compete for binding of the antisera to the immobilized protein is compared to the ability of the hHAC3 encoded by SEQ ID NO:1 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of hHAC3, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by hHAC3 that is required to inhibit 50% of binding, then the second protein is said to specifically bind to the polyclonal antibodies generated to the respective hHAC3 immunogen.

Other Assay Formats

Western blot (immunoblot) analysis is used to detect and quantify the presence of the hHAC3 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind hHAC3. The anti-hHAC3 antibodies specifically bind to hHAC3 on the solid support. These antibodies may be directly labeled or alternatively may be subsequently detected using labeled antibodies (e.g., labeled sheep anti-mouse antibodies) that specifically bind to the anti-hHAC3 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., Amer. Clin. Prod. Rev. 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize hHAC3, or secondary antibodies that recognize anti-hHAC3 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of hHAC3

A. Assays

Human HAC3 monomers and hHAC3 alleles and polymorphic variants are subunits of hyperpolarization-activated cation channels. The activity of a cation channel comprising hHAC3 can be assessed using a variety of in vitro and in vivo assays, e.g., measuring current, measuring membrane potential, measuring ion flux, e.g., potassium, sodium, guanidinium, and rubidium, measuring potassium or other cation concentration, measuring second messengers and transcription levels, using potassium-dependent yeast growth assays, measuring ligand binding, and using e.g., voltage-sensitive dyes, radioactive tracers, and patch-clamp electrophysiology. hHAC polypeptides and channels can be attached to a solid substrate, in solution, or expressed in a cell or cell membrane that is attached to a solid substrate or in solution. Channels made of HAC family members are typically blocked by about 2 mM cesium.

Furthermore, such assays can be used to test for inhibitors and activators of channels comprising hHAC3. Such modulators of a hyperpolarization-activated cation channel are useful for treating various disorders involving cation channels. Treatment of dysfunctions include pacemaker dysfunctions such as familial sinus rhythm diseases, sick sinus syndrome associated with atrial fibrillation, and ventricular arrhythmias, memory and learning disorders, sleeping disorders, bipolar disease, schizophrenia, as well as CNS disorders such as migraines, hearing and vision problems, seizures, and as neuroprotective agents (e.g., to prevent stroke). Such modulators are also useful for investigation of the channel diversity provided by hHAC3 and the regulation/modulation of cation channel activity provided by hHAC3.

Modulators of the hyperpolarization-activated cation channels are tested using biologically active hHAC3, either recombinant or naturally occurring. Human HAC3 can be isolated, expressed in a cell, or expressed in a membrane derived from a cell. In such assays, hHAC3 is expressed alone to form a homomeric cation channel or is co-expressed with a second alpha subunit (e.g., HAC1 or HAC2) so as to form a heteromeric cation channel. HAC can also be expressed with additional beta subunits. Modulation is tested using one of the in vitro or in vivo assays described above. Samples or assays that are treated with a potential cation channel inhibitor or activator are compared to control samples without the test compound, to examine the extent of modulation. Control samples (untreated with activators or inhibitors) are assigned a relative cation channel activity value of 100. Inhibition of channels comprising hHAC3 is achieved when the cation channel activity value relative to the control is about 90%, preferably 50%, more preferably 25–0%. Activation of channels comprising hHAC3 is achieved when the cation channel activity value relative to the control is 110%, more preferably 150%, more preferable 200% higher. Compounds that increase the flux of ions will cause a detectable increase in the ion current density by increasing the probability of a channel comprising hHAC3 being open, by decreasing the probability of it being closed, by increasing conductance through the channel, and/or by allowing the passage of ions.

Changes in ion flux may be assessed by determining changes in polarization (i.e., electrical potential) of the cell or membrane expressing the cation channel comprising hHAC3. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium, sodium, or guanidinium flux assays and fluorescence assays using voltage-sensitive dyes or ion-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising hHAC3 can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of cations such as potassium, sodium, guanidinium, or rubidium ions. The cations can be measured in a variety of standard ways. They can be measured directly by concentration changes of the ions or indirectly by membrane potential or by radio-labeling of the ions. Ligand binding to the channel or polypeptide can be measured by standard assays known to those of skill in the art. Consequences of the test compound on ion flux can be quite varied. Accordingly, any suitable physical, chemical or physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

Preferably, the HAC3 that is a part of the hyperpolarization-activated cation channel used in the assay will have the sequence displayed in SEQ ID NO:1 or a conservatively modified variant thereof. Alternatively, the HAC3 of the assay will be derived from a eukaryote and include an amino acid subsequence having amino acid sequence identity to hHAC3. Generally, the amino acid sequence identity will be at least 96%, preferably at least 98%, most preferably at least 99%.

Human HAC3 orthologs will generally confer substantially similar properties on a channel comprising such hHAC3, as described above. In a preferred embodiment, the cell placed in contact with a compound that is suspected to be a hHAC3 homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to hHAC3 are considered homologs or orthologs of hHAC3.

B. Modulators

The compounds tested as modulators of HAC channels comprising a human HAC3 subunit can be any small chemical compound, or a biological entity, such as a protein, sugar, nucleic acid or lipid. Alternatively, modulators can be genetically altered versions of a human HAC3 subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al, *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science,* 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a HAC3 channel comprising a human HAC3 subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100– about 1500 different compounds. It is possible to assay several different plates per day; assay screens for up to about 6,000–20,000 different compounds is possible using the integrated systems of the invention. More recently, microfluidic approaches to reagent manipulation have been developed.

C. Solid State and Soluble High Throughput Assays

In one embodiment the invention provide soluble assays using potassium channels comprising hHAC3; a membrane comprising a channel comprising hHAC3, or a cell or tissue expressing channels comprising hHAC3, either naturally occurring or recombinant. In another embodiment, the invention provides solid phase based in vitro assays in a high throughput format, where hHAC3 channel attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100– about 1500 different compounds. It is possible to assay many plates per day; assay screens for up to about 6,000, 20,000, 50,000, or more than 100,000 different compounds is possible using the integrated systems of the invention.

The channel of interest, or a cell or membrane comprising the channel of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:6031–6040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753–759 (1996) (all describing arrays of biopolymers fixed to solid substrates). Non-chemical approaches for fixing tag binders to substrates include other common methods, such as heat, cross-linking by UV radiation, and the like.

VII. Computer Assisted Drug Design Using hHAC3

Yet another assay for compounds that modulate the activities of hHAC3 involves computer assisted drug design, in which a computer system is used to generate a three-dimensional structure of hHAC3 based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other cation channel subunits. These regions are then used to identify ligands that bind to the protein or region where hHAC3 interacts with other cation channel subunits.

The three-dimensional structural model of the protein is generated by entering channel protein amino acid sequences of at least 25–75 amino acid residues or corresponding nucleic acid sequences encoding a hHAC3 monomer into the computer system. The amino acid sequence of each of the monomers is selected from the group consisting of SEQ ID NO:1 and a conservatively modified versions thereof. The amino acid sequence represents the primary sequence or subsequence of each of the proteins, which encodes the structural information of the protein. At least 25–75 residues of the amino acid sequence (or a nucleotide sequence encoding 25–75 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of hHAC3 protein to identify ligands that bind to hHAC3. Binding affinity between the protein and ligands is determined using energy terms to determine which ligands have an enhanced probability of binding to the protein.

Computer systems are also used to screen for mutations, polymorphic variants, alleles and interspecies homologs of hHAC3 genes. Such mutations can be associated with disease states. Once the variants are identified, diagnostic assays can be used to identify patients having such mutated genes associated with disease states. Identification of the mutated hHAC3 genes involves receiving input of a first nucleic acid, e.g., SEQ ID NO:2, or an amino acid sequence encoding hHAC3, selected from the group consisting of SEQ ID NO:1, and a conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in hHAC3 genes, and mutations associated with disease states. The first and second sequences described above can be saved on a computer readable substrate.

Human HAC3 monomers and the hyperpolarization-activated cation channels containing these hHAC3 monomers can be used with high density oligonucleotide array technology (e.g., GeneChip™) to identify homologs and polymorphic variants of hHAC3 in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. Cellular Transfection and Gene Therapy

The present invention provides the nucleic acids of hHAC3 for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for hHAC3, under the control of a promoter, then expresses a hHAC3 monomer of the present invention, thereby mitigating the effects of absent, partial inactivation, or abnormal expression of the hHAC3 gene. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfier & Böhm eds., 1995); and Yu et al., *Gene Therapy* 1:13–26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, TIBTECH 11:211–217 (1993); Mitani & Caskey, TIBTECH 11:162–166 (1993); Dillon, TIBTECH 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfler and Böhm (eds) (1995); and Yu et al., *Gene Therapy* 1:13–26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al, *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin, et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al, *Blood* 85:3048–305 (1995); Kohn et al, *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors. (Ellem et al., *Immunol Immunother.* 44(1):10–20 (1997); Dranoffetal., *Hum. Gene Ther.* 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al, *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al, *Hum. Gene Ther.* 7:1083–9 (1998)). Additional examples of the use of adenovirus vectors for gene transfer in clinical trials include Rosenecker et al., *Infection* 241: 5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., Remington's Pharmaceutical Sciences, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the HAC3 channels comprising a human HAC3 alpha subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Transduced cells are prepared for reinfusion according to established methods (see Abrahamsen et al., *J. Clin. Apheresis* 6:48–53 (1991); Carter et al., *J. Clin. Apheresis* 4:113–117 (1998); Aebersold et al., *J. Immunol. Meth.* 112:1–7 (1998); Muul et al., *J. Immunol. Methods* 101: 171–181 (1987); and Carter et al., *Transfusion* 27:362–365 (1987)). After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

X. Kits

Human HAC3 and its homologs are useful tools for examining expression and regulation of hyperpolarization-activated cation channels. Human HAC3-specific reagents that specifically hybridize to hHAC3 nucleic acid, such as hHAC3 probes and primers, and hHAC3-specific reagents that specifically bind to the hHAC3 protein, e.g., hHAC3 antibodies are used to examine expression and regulation.

Nucleic acid assays for the presence of hHAC3 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, hHAC3 protein can be detected with the various immunoassay techniques described above. The test sample is typically compared to both a positive control (e.g., a sample expressing recombinant hHAC3 monomers) and a negative control.

The present invention also provides for kits for screening modulators of the heteromeric potassium channels. Such kits can be prepared from readily available materials and reagents. For example, such kits can comprise any one or more of the following materials: hHAC3 monomers, reaction tubes, and instructions for testing the activities of hyperpolarization-activated cation channels containing hHAC3. A wide variety of kits and components can be prepared according to the present invention, depending upon the intended user of the kit and the particular needs of the user. For example, the kit can be tailored for in vitro or in vivo assays for measuring the activity of a hyperpolarization-activated cation channel comprising a hHAC3 monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLE

The following example is provided by way of illustration only and not by way of limitation. Those of skill in the art will readily recognize a variety of noncritical parameters that could be changed or modified to yield essentially similar results.

Example I:

Isolation of Nucleic Acids Encoding hHAC3 and Functional Analysis of Hyperpolarization-Activated Cation Channels Containing hHAC3

Using PCR and primers, according to standard conditions, hHAC3 was amplified from a human hippocampus cDNA library. The following degenerate primers were used for amplification of hHAC3:

(1) 5-TGGGAGGAGATCTTYCAYATGACNTAYGA-3   (SEQ ID NO:7)

(2) 5-CGTCTCGAATGCCCKNCKCATCATNGG-3   (SEQ ID NO:8)

Primers (1) and (2) were used together to amplify portions of the region that encode the S4 and putative cyclic-nucleotide binding domains of hyperpolarization-activated cation channels. PCR conditions were as follows: 95 degrees for 15 seconds, 60–40 degrees for 15 seconds, 72 degrees for 45 seconds. The reaction was run for 40 cycles.

5' and 3' RACE PCR was subsequently used to clone the complete ends of the hHAC3 gene from hippocampal cDNA. The Clontech Marathon RACE kit was used for this procedure. A gene specific oligo is used in combination with a non-selective oligo tagged to the cDNA end. Two rounds of 5' RACE were performed. In the first round, the gene specific primer was CCTGCTGCCCATAGCCAATGCA-CAGC (SEQ ID NO:9). In the second round, the first reaction was reamplified with the nested gene-specific primer GCACCACGAACTGCAGACAGCCATC (SEQ ID NO:10). For the 3' RACE, four nested rounds were performed with the following gene specific primers:

GTTCTCACCAAGCTGCGCTTTGAGGTC              (SEQ ID NO:11)

CCAGCATGGGCTGCTCAGTGTGCTG                (SEQ ID NO:12)

GCCCACTCTCAGCCTCCCAACCCTC                (SEQ ID NO:13)

CCCAACCAAGCTTGCCTCAGCGGGCAACAGGCGATGG    (SEQ ID NO:14)

The sequence of the degernerate PCR product and the 5' and 3' RACE product were overlapped to produce a contiguous HAC3 sequence spanning the entire coding region. The entire coding region can be amplified in a single fragment using primers SEQ ID NO:3 and 6. The nucleotide and amino acid sequences of hHAC3 are provided, respectively, in SEQ ID NO:2 and SEQ ID NO:1.

Human HAC3 monomer was expressed according to standard methodology in oocytes to demonstrate its ability to form cation channels. HAC3 expresses a cation channel that opens upon hyperpolarization when expressed in *Xenopus* oocytes. The current activates over several seconds at voltage steps more hyperpolarized than −80 mV, with little or nor inactivation. The reversal potential of the current lies between −30 and −40 mV, indicating that HAC3 is a classic $I_h$ channel that passes both sodium and potassium. HAC3 is distinct from other $I_h$ channels in that its activation is particularly slow and occurs at more hyperpolarized potentials.

Human HAC3 expression patterns were analyzed using northern blots and mRNA dot blots. Human HAC3 expression was especially high in the putamen, thalamus, caudate nucleus, medulla, occipital lobe, substantia nigra, spinal cord and fetal brain.

Human HAC3 was also expressed at moderate levels in several tissues, such as the amygdala, cerebellum, cerebral cortex, frontal lobe, hippocampus, temporal lobe, nucleus accumbens, heart, stomach, pancreas, pituitary gland, liver and appendix. The colon and small intestine displayed much higher expression when measured with mRNA dot blots than with northern blots. Low to trace levels of expression were found in tissues such as prostate, testis, adrenal, thyroid gland, salivary gland, kidney, spleen, thymus, bone marrow, lung trachea, placenta, aorta, skeletal muscles, bladder, uterus, ovary, mammary glands, peripheral leukocytes and many fetal tissues.

What is claimed is:

1. An isolated nucleic acid encoding a polypeptide comprising an alpha subunit of a cation channel, the polypeptide forming, with at least one additional hyperpolarization-activated channel (HAC) alpha subunit, a cation channel having the characteristic of activation upon hyperpolarization; wherein said nucleic acid encodes a polypeptide that has greater than 96% identity to SEQ ID NO:1.

2. The isolated nucleic acid of claim 1, wherein the nucleic acid encodes an amino acid sequence of SEQ ID NO:1.

3. The isolated nucleic acid sequence of claim 1, wherein the nucleic acid has a nucleotide sequence of SEQ ID NO:2.

4. The isolated nucleic acid of claim 1, wherein the nucleic acid is a splice variant of SEQ ID NO:2.

5. The isolated nucleic acid of claim 1, wherein the nucleic acid encodes a polypeptide having a molecular weight of between about 85 kDa to about 95 kDa.

6. The isolated nucleic acid of claim 1, wherein the polypeptide comprises an alpha subunit of a homomeric cation channel.

7. The isolated nucleic acid of claim 1, wherein the polypeptide comprises an alpha subunit of a heteromeric cation channel.

8. The isolated nucleic acid of claim 1, wherein the nucleic acid encodes a polypeptide having an amino acid sequence that has greater than 96% identity to SEQ ID NO:1.

9. An expression vector comprising the nucleic acid of claim 1.

10. A host cell transfected with the vector of claim 9.

* * * * *